United States Patent
Okabe et al.

(10) Patent No.: US 8,135,507 B2
(45) Date of Patent: Mar. 13, 2012

(54) DRIVER CONDITION ESTIMATION APPARATUS, SERVER, DRIVER INFORMATION COLLECTING APPARATUS, AND DRIVER CONDITION ESTIMATION SYSTEM

(75) Inventors: Nobuyuki Okabe, Toyota (JP); Naoki Taki, Okazaki (JP); Akira Nagae, Susono (JP); Yasushi Kusaka, Toyota (JP); Shinya Furuta, Toyota (JP); Takahiro Matsunaga, Mishima (JP); Hiroaki Seguchi, Toyota (JP)

(73) Assignee: Toyota Jidosha Kabushiki Kaisha, Aichi (JP)

( * ) Notice: Subject to any disclaimer, the term of this patent is extended or adjusted under 35 U.S.C. 154(b) by 435 days.

(21) Appl. No.: 12/513,076

(22) PCT Filed: Nov. 5, 2007

(86) PCT No.: PCT/JP2007/071500
§ 371 (c)(1),
(2), (4) Date: Apr. 30, 2009

(87) PCT Pub. No.: WO2008/059727
PCT Pub. Date: May 22, 2008

(65) Prior Publication Data
US 2010/0030434 A1 Feb. 4, 2010

(30) Foreign Application Priority Data
Nov. 15, 2006 (JP) .................. 2006-309460

(51) Int. Cl.
*B60K 28/06* (2006.01)
*G08B 23/00* (2006.01)

(52) U.S. Cl. .............. 701/29; 701/1; 701/2; 701/35; 340/439; 340/576; 180/272

(58) Field of Classification Search .............. 701/1, 2, 701/29, 35; 340/438, 439, 576; 180/272
See application file for complete search history.

(56) References Cited

U.S. PATENT DOCUMENTS

| | | | | |
|---|---|---|---|---|
| 5,821,860 A | * | 10/1998 | Yokoyama et al. | 340/576 |
| 5,832,400 A | | 11/1998 | Takahashi et al. | |
| 6,060,989 A | * | 5/2000 | Gehlot | 340/576 |
| 6,599,243 B2 | * | 7/2003 | Woltermann et al. | 600/300 |
| 6,946,966 B2 | | 9/2005 | Koenig | |
| 6,960,168 B2 | * | 11/2005 | Yanagidaira et al. | 600/300 |
| 6,974,414 B2 | * | 12/2005 | Victor | 600/300 |
| 7,117,075 B1 | | 10/2006 | Larschan et al. | |
| 7,206,631 B2 | * | 4/2007 | Kawachi et al. | 600/519 |
| 7,956,730 B2 | * | 6/2011 | White et al. | 340/426.2 |
| 2002/0120374 A1 | * | 8/2002 | Douros et al. | 701/29 |
| 2002/0183006 A1 | | 12/2002 | Yasushi et al. | |
| 2004/0089491 A1 | | 5/2004 | Reuter | |
| 2004/0212506 A1 | | 10/2004 | Cherouny et al. | |

(Continued)

FOREIGN PATENT DOCUMENTS
JP 06-199157 A 7/1994
(Continued)

*Primary Examiner* — Ruth Ilan
(74) *Attorney, Agent, or Firm* — Sughrue Mion, PLLC

(57) ABSTRACT

A driver condition estimation apparatus 5 estimates condition of a driver. The driver condition estimation apparatus 5 includes a driver condition estimating unit 50*a* for estimating the condition of the driver before the driver starts driving; and a control variable changing unit 50*b* for changing control variables of in-vehicle devices based on the condition of the driver estimated by the driver condition estimating unit 50*a*.

10 Claims, 17 Drawing Sheets

U.S. PATENT DOCUMENTS

| | | |
|---|---|---|
| 2004/0225419 A1 | 11/2004 | Sakai et al. |
| 2005/0030184 A1 | 2/2005 | Victor |
| 2005/0125117 A1 | 6/2005 | Breed |
| 2005/0137753 A1 | 6/2005 | Basson et al. |
| 2007/0296601 A1 * | 12/2007 | Sultan et al. .................. 340/576 |

FOREIGN PATENT DOCUMENTS

| | | |
|---|---|---|
| JP | 06-206473 A | 7/1994 |
| JP | 08-072591 A | 3/1996 |
| JP | 10-288532 A | 10/1998 |
| JP | 11-039592 A | 2/1999 |
| JP | 2002-353976 A | 12/2002 |
| JP | 2003-048449 A | 2/2003 |
| JP | 2003-123198 A | 4/2003 |
| JP | 2004-097496 A | 4/2004 |
| JP | 2004-106716 A | 4/2004 |
| JP | 2004-213130 A | 7/2004 |
| JP | 2004-271335 A | 9/2004 |
| JP | 2005-003592 A | 1/2005 |
| JP | 2005-143895 A | 6/2005 |
| JP | 2005-168856 A | 6/2005 |
| JP | 2005-173989 A | 6/2005 |
| JP | 2005-210361 A | 8/2005 |
| JP | 2005-284771 A | 10/2005 |
| JP | 2006-247255 A | 9/2006 |

* cited by examiner

FIG.4

○MONTH ○DAY
BEFORE-BOARDING BEHAVIOR INFORMATION

| THINGS-FORGOT-TO -BRING INFORMATION | WALLET |
|---|---|
| DOOR INFORMATION | FORGOT TO LOCK |
| ELECTRIC APPLIANCE INFORMATION | FORGOT TO TURN OFF FLUORESCENT LAMP |

(a) ○MONTH ○DAY
DURING-BOARDING BEHAVIOR INFORMATION

| THROWING OF BAGGAGE | YES |
|---|---|
| DOOR OPENING/ CLOSING SPEED | HIGH |
| TIME LAG BETWEEN DOOR OPENING AND ENGINE START | SHORT |

(b) ○MONTH ○DAY
IN-VEHICLE BEHAVIOR INFORMATION

| INTER-VEHICLE DISTANCE | SMALL |
|---|---|
| IGNORING TRAFFIC LIGHT | YES |
| ACCELERATION | HIGH |

FIG.16

○MONTH ○DAY
SLEEPINESS FACTOR INFORMATION

| SLEEPING TIME | 7h |
|---|---|
| SOUND INFORMATION | SNORING LEVEL 3<br>AMBIENT NOISE LEVEL 2 |

# DRIVER CONDITION ESTIMATION APPARATUS, SERVER, DRIVER INFORMATION COLLECTING APPARATUS, AND DRIVER CONDITION ESTIMATION SYSTEM

TECHNICAL FIELD

The present invention generally relates to a driver condition estimation apparatus, a server, a driver information collecting apparatus, and a driver condition estimation system for controlling a vehicle based on an estimated condition of a driver.

BACKGROUND ART

While driving a vehicle, the driver often becomes irritated worrying about, for example, a meeting time or time of arrival at a destination. Although it varies from person to person, the driver tends to become irritated without noticing and such irritation generally has adverse effects on driving. For example, patent document 1 discloses a device that determines whether the driver is irritated and calms down the driver if he/she is irritated. The disclosed device detects the moving distance and the number of movements of the driver using a temperature sensor, determines that the driver is irritated if the moving distance or the number of movements exceeds a threshold, and calms down the driver by playing music or emitting a fragrance.

Thus, the device disclosed in patent document 1 determines whether the driver is irritated by detecting physical movements of the driver using the temperature sensor. However, it may become difficult to detect the temperature of the driver if the ambient temperature becomes high.

Meanwhile, psychological and physical condition of the driver starts affecting the driver before the driver starts driving and cause actual problems during driving. However, no technology has been proposed to detect the psychological and physical condition of the driver before the driver starts driving. Thus, with related-art technologies, it is not possible to detect the psychological and physical condition of the driver before the driver starts driving and therefore it is difficult to provide appropriate driving assistance in time.

[Patent document 1] Japanese Patent Application Publication No. 2004-106716

DISCLOSURE OF INVENTION

Problems to be Solved by the Invention

One object of the present invention is to provide a driver condition estimation apparatus, a server, a driver information collecting apparatus, and a driver condition estimation system that can estimate the condition of a driver before the driver starts driving.

Means for Solving the Problems

An aspect of the present invention provides a driver condition estimation apparatus for estimating condition of a driver. The driver condition estimation apparatus includes a driver condition estimating unit configured to estimate the condition of the driver before the driver starts driving; and a control variable changing unit configured to change control variables of in-vehicle devices based on the condition of the driver estimated by the driver condition estimating unit.

This configuration makes it possible to estimate the condition of the driver before the driver starts driving and thereby to provide appropriate driving assistance from when the driver starts driving.

According to another aspect of the present invention, the driver condition estimation apparatus also includes an at-home driver information receiving unit configured to receive at-home driver information (for example, at least one of before-boarding behavior information and during-boarding behavior information) obtained at a home of the driver. In this case, the driver condition estimating unit estimates the condition of the driver based on the at-home driver information. This configuration makes it possible to estimate the condition of the driver based on information of the driver obtained at home.

Advantageous Effect of the Invention

Aspects of the present invention make it possible to provide a driver condition estimation apparatus, a server, a driver information collecting apparatus, and a driver condition estimation system that can estimate the condition of a driver before the driver starts driving.

BRIEF DESCRIPTION OF THE DRAWINGS

FIG. 4 is a table showing exemplary before-boarding behavior information stored in a memory;

FIG. 16 is a table showing exemplary sleepiness factor information stored in a memory.

EXPLANATION OF REFERENCES

Figure 1:
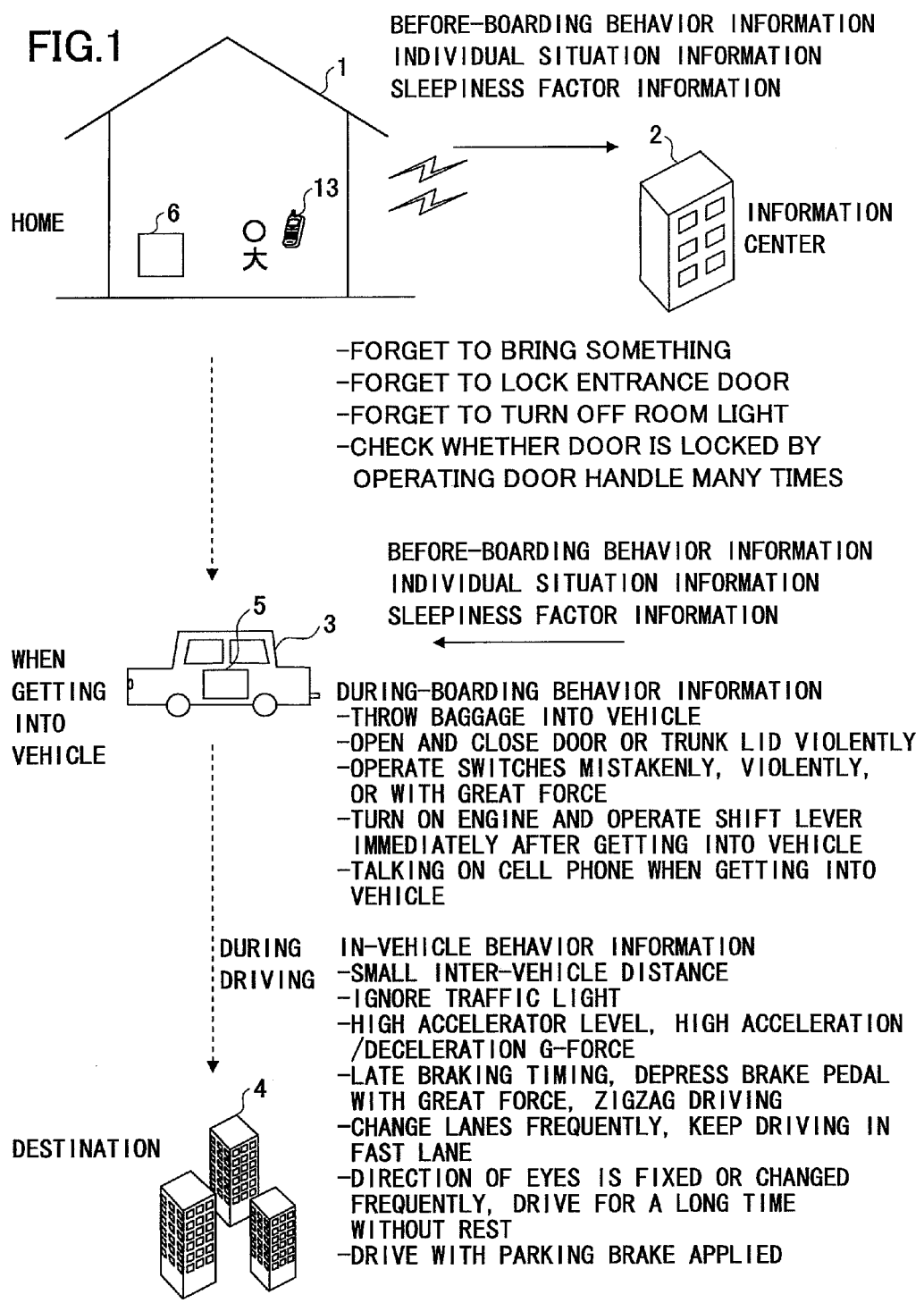
FIG. 1 is a drawing outlining a process of estimating the condition of a driver.

1 Home
2 Information center
3 Vehicle
4 Destination
5 Driver condition estimation apparatus
6 Driver information collecting apparatus
7 Server
8 Base station
11 Sensors
50 Driver condition estimation device
50a, 71a Driver condition estimating unit
50b Control variable changing unit
60 Information collecting device
60a Driver information collecting unit

BEST MODE FOR CARRYING OUT THE INVENTION

The best mode for carrying out the invention is described based on the following embodiments with reference to the accompanying drawings.

First Embodiment

FIG. 1 is a drawing outlining a process of estimating the condition of a driver. Here, it is assumed that the driver lives in a home 1, gets into a vehicle 3, and drives the vehicle 3 to go to a destination 4 such as a place of work or a leisure facility. A driver condition estimation apparatus of this embodiment estimates the condition (for example, psychological condition such as irritation) of the driver based on the behavior (behavioral events) of the driver detected while the driver is at the home 1, getting into the vehicle 3, or driving the vehicle 3. If it is determined that the driver is irritated, the driver condition estimation apparatus sets characteristics of the vehicle 3 on the safe and environmentally-friendly side to reduce the influence of irritation on driving. When it is determined that the driver has calmed down, the driver condition estimation apparatus resets the characteristics of the vehicle 3. Since the driver condition estimation apparatus can detect irritation of the driver based on the behavior of the driver at the home 1, i.e., before driving, the driver condition estimation apparatus can start controlling the vehicle 3 on the safe and environmentally-friendly side just when the driver starts driving.

First, exemplary situations that cause irritation (irritating situations) and exemplary behavior of the driver indicating the irritating situations are described. Here, it is assumed that people tend to become irritated when pressed for time.

a. Irritating Situations at Home 1

Left home late; overslept; forgot to bring something; have something to worry about; keeping someone waiting b. Irritating Situations when Getting into Vehicle 3

In a hurry; forgot to operate something; violent manner c. Irritating Situations During Driving Being late for an appointment; pressed for time; car in front is slow; front view is blocked by a truck; traffic is heavy; being lost; wondering whether it is possible to pass through an intersection before the traffic light changes Whether the driver is irritated may be determined by detecting situations as described above based on the behavior of the driver.

A. Behavior Indicating Irritation of Driver to be Detected at Home 1

Forget to bring something; forget to lock the entrance door; forget to turn off the room light; check whether the door is locked by operating the door handle many times B. Behavior Indicating Irritation of Driver to be Detected when Driver Gets into Vehicle Throw baggage into vehicle; open and close the door or the trunk lid violently (very quickly); operate switches mistakenly, violently, or with great force; turn on the engine immediately after getting into the vehicle; talking on the cell phone when getting into the vehicle C. Behavior Indicating Irritation of Driver to be Detected During Driving Inter-vehicle distance is small; ignore traffic light (cross the intersection while the traffic light is yellow); accelerator level is high and acceleration/deceleration G-force is high; braking timing is late and brake pedal is depressed with great force; zigzag driving; change lanes frequently; keep driving in the fast lane; direction of eyes is fixed or changed frequently; drive for a long time without rest; drive with the parking brake applied Behavior as described in A through C is often seen when the driver is irritated (or in a hurry). Therefore, whether the driver is irritated can be determined by detecting such behavior of the driver.

The home 1 includes a driver information collecting apparatus 6 for detecting the behavior of the driver. The driver information collecting apparatus 6 obtains before-boarding behavior information on the behavior of the driver as described in "A" and sends the before-boarding behavior information via an information center 2 to the vehicle 3. The vehicle 3 includes a driver condition estimation apparatus 5 for estimating the condition of the driver. The driver condition estimation apparatus 5 obtains during-boarding behavior information and in-vehicle behavior information on the behavior of the driver as described in "B" and "C" and determines whether the driver is irritated and/or the level of irritation based on the during-boarding behavior information, the in-vehicle behavior information, and the before-boarding behavior information received from the information center 2.

Figure 2:
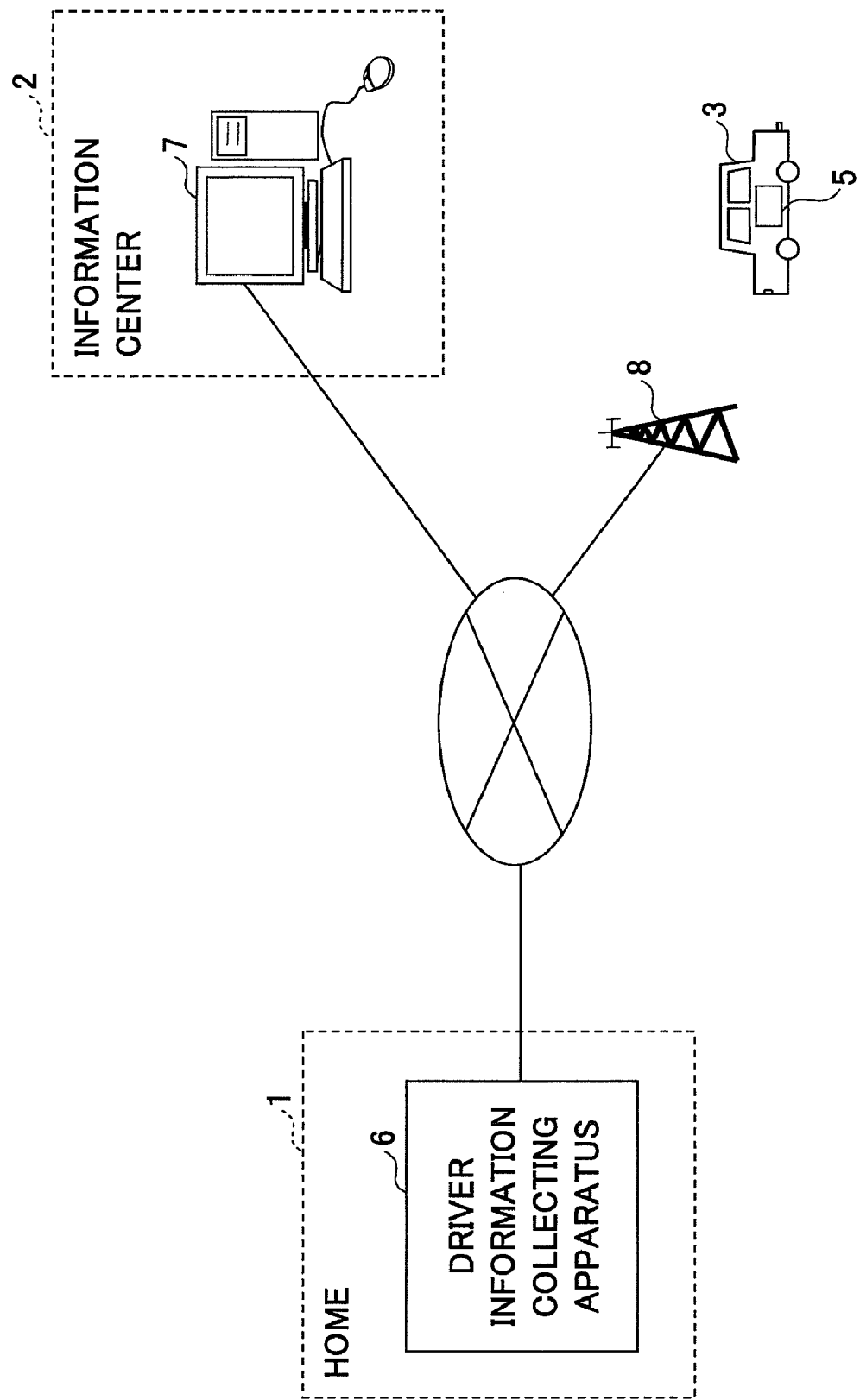
FIG. 2 is a drawing illustrating an exemplary configuration of a driver condition estimation system for estimating the condition of a driver.

FIG. 2 is a drawing illustrating an exemplary configuration of a driver condition estimation system for estimating the condition of a driver. In the driver condition estimation system, the driver information collecting apparatus 6 and a server 7 of the information center 2 are connected via a network, and the driver condition estimation apparatus 5 is connected via a wireless or wired communication link to a base station 8 connected to the network. The network is implemented, for example, by a wired network such as a public switched telephone network (PSTN), an integrated services digital network (ISDN), or a fiber optic network; or a wireless network such as a cell-phone network, a personal handy-phone system (PHS) network, a wireless LAN, or a worldwide interoperability for microwave access (WiMAX) system.

The driver information collecting apparatus 6, the server 7, and the driver condition estimation apparatus 5 communicate with each other according to the point to point protocol (PPP). Higher-layer protocols such as the transmission control protocol/Internet protocol (TCP/IP) and the hypertext transfer protocol (HTTP) and the file transfer protocol (FTP) that are upward compatible with TCP/IP are implemented on the data link established by the PPP. In other words, data communication is enabled via a network such as the Internet or a wide area network (WAN).

[A. Behavior Indicating Irritation of Driver to be Detected at Home 1]

Figure 3:
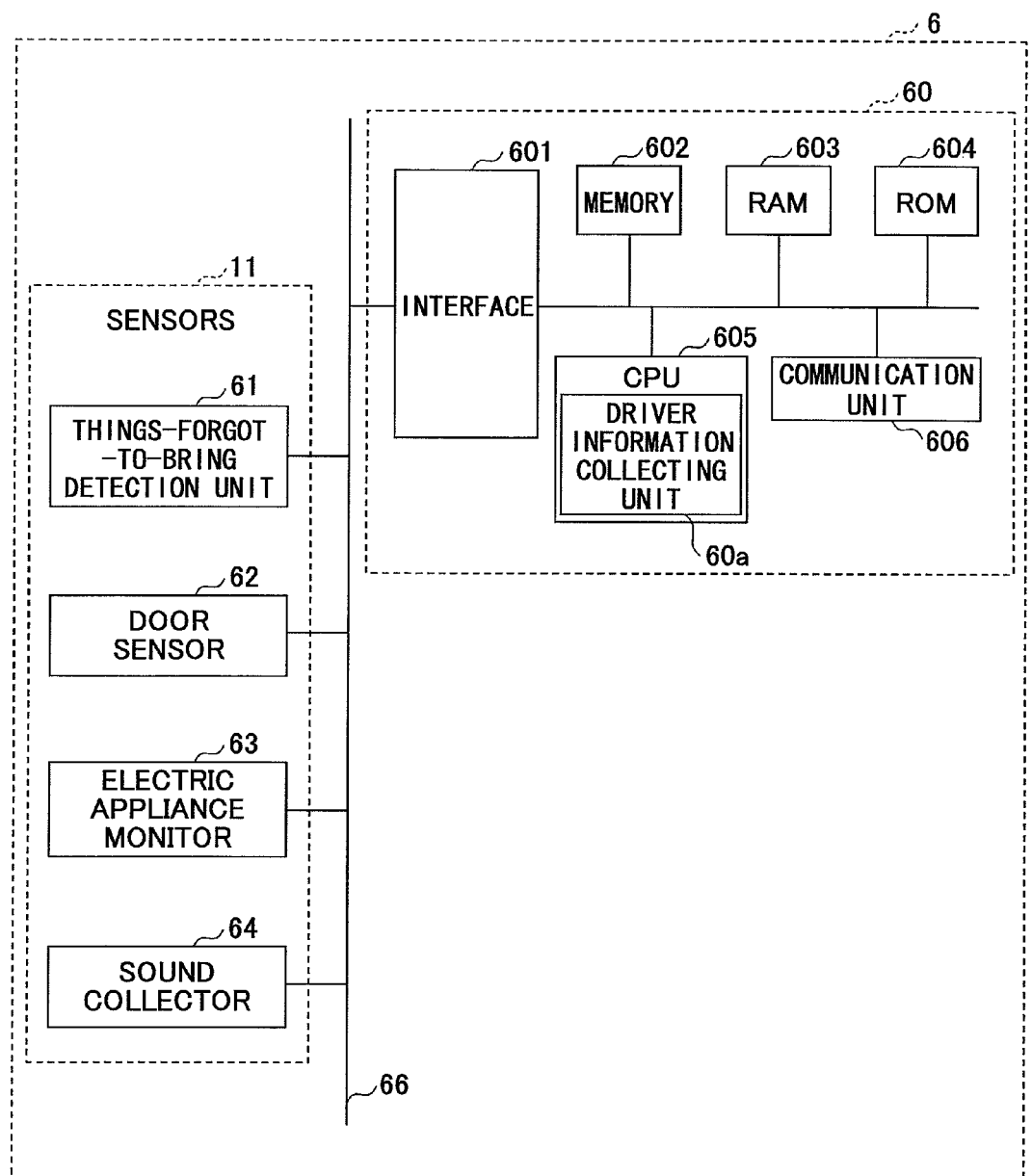
FIG. 3 is a block diagram illustrating a configuration of a driver information collecting apparatus.

FIG. 3 is a block diagram illustrating a configuration of the driver information collecting apparatus 6. The driver information collecting apparatus 6 includes sensors 11 for detecting the behavior of the driver and an information collecting device 60 connected via a network such as a LAN to the sensors 11.

The sensors 11 include, for example, a things-forgot-to-bring detection unit 61, a door sensor 62, an electric appliance monitor 63, and a sound collector 64. The things-forgot-to-bring detection unit 61 detects whether any one of small belongings such as a cell phone, a key of the home 1, a key of the vehicle 3, a wallet, a commuter pass, and an ID card, which the driver normally brings with him/her, is left in the home 1 when the driver goes out. For example, the things-forgot-to-bring detection unit 61 transmits a request radio signal, determines whether an IC chip embedded in each of the belongings responds to the request radio signal, and thereby determines whether the belongings are in the home 1. A transmitter of the request radio signal is provided in the entrance hall. When the presence of the driver in the entrance hall (that the driver is going to leave) is detected by, for example, an infrared sensor or a floor pressure sensor, the things-forgot-to-bring detection unit 61 determines whether the IC chip of each of the belongings responds to the request radio signal and thereby determines whether any of the belongings is left behind. The belongings to be brought with the driver may be registered in the things-forgot-to-bring detection unit 61 in advance. Alternatively, the things-forgot-to-bring detection unit 61 may be configured to store belongings that are brought with the driver and to determine belongings that must be brought with the driver based on past statistical data.

The door sensor 62 detects opening and closing of the door of the home 1 and also detects whether the door is locked. For example, a switch that outputs an ON signal when the door is locked may be provided for the lock of the door. If the ON signal is not output after the door is closed, the door sensor 62 determines that the driver has forgotten to lock the door. Meanwhile, when a smart key system is used for the door lock, the door sensor 62 may be configured to detect whether the door is locked based on functions of the smart key. In a smart key system, key detection areas are defined inside and outside of the entrance. If the driver carries a smart key when leaving home, the smart key is detected in the key detection area inside of the entrance. When the driver exits the front door, the smart key is detected in the key detection area outside of the entrance. Then, when the driver leaves the key detection area, the door is automatically locked. Accordingly, if the driver gets out of the door without the smart key, no smart key is detected in the key detection area outside of the entrance and the door is not locked (even in this case, the door may be automatically locked after a while). When this happens, the door sensor 62 determines that the driver has forgotten to lock the door (or has forgotten to bring the smart key).

The electric appliance monitor 63 monitors statuses of electric appliances such as a fluorescent lamp and a television. If an electric appliance such as a fluorescent lamp, a television, an air conditioner, or a stereo is still turned on after the driver leaves the home 1, the electric appliance monitor 63 determines that the driver has forgotten to turn off the electric appliance.

The sound collector 64 detects sounds made by the driver or family members and outside noise with microphones installed in various places inside and outside of the home 1 and determines the influence of such sounds on the driver. When a sound is detected by a microphone, the sound collector 64 obtains the level and location of the sound. Also, the sound collector 64 preferably includes a voice recognition function for recognizing words spoken by the driver.

The information collecting device 60 includes a CPU 605 for executing programs, a memory 602 for storing the before-boarding behavior information obtained by the sensors 11 and programs, a ROM 604 for storing an operating system and device programs, a RAM 603 used as a work area for temporarily storing programs, and a communication unit 606 such as a network interface card (NIC) for connecting the driver information collecting apparatus 6 to the network. These components are connected to each other via a bus. A driver information collecting unit 60a is implemented by executing a program by the CPU 605.

The information collecting device 60 is connected via an interface 601 to the sensors 11 and collects before-boarding behavior information from the sensors 11. The interface 601 may be implemented by the same NIC of the communication unit 606 and configured to receive the before-boarding behavior information sent from the sensors 11 to an IP address assigned to the interface 601. Alternatively, the interface 601 may be implemented by a data logger that receives the before-boarding behavior information from the sensors 11.

The driver information collecting unit 60a stores the before-boarding behavior information sent from the sensors 11 in the memory 602. FIG. 4 is a table showing exemplary before-boarding behavior information stored in the memory 602. The driver information collecting unit 60a receives before-boarding behavior information each time when the sensors 11 detect the behavior of the driver. Since information obtained just before the driver gets into the vehicle 3 is needed as the before-boarding behavior information, the driver information collecting unit 60a, for example, stores one day of before-boarding behavior information in the memory 602. In the example shown in FIG. 4, "wallet" is stored as things-forgot-to-bring information, "forgot to lock" is stored as door information, and "forgot to turn off fluorescent lamp" is stored as electric appliance information. Here, it is assumed that as the number of detected behavioral events increases, the level of irritation of the driver increases. The before-boarding behavior information may instead be represented by a table listing all detectable behavioral events with flags that are turned on when the corresponding behavioral events are detected.

The driver information collecting unit 60a transmits the before-boarding behavior information obtained by the sensors 11 to the information center 2 when the driver leaves the home 1. Although the driver information collecting unit 60a may be configured to determine whether the driver is irritated according to a method as described below, the determination is preferably performed at the vehicle 3 taking also into account the during-boarding behavior information and the in-vehicle behavior information.

The information center 2 is described below. The server 7 of the information center 2 intermediates between the driver information collecting apparatus 6 and the vehicle 3 and thereby provides various services for the driver. For example, the information center 2 detects the intrusion into the vehicle 3 or the start of the engine by a third person and reports the detected event to a registered email address of a mobile terminal 13 of the driver. Also, the information center 2 enables the driver to remote-control a device on the vehicle 3 using the mobile terminal 13.

Figure 5:
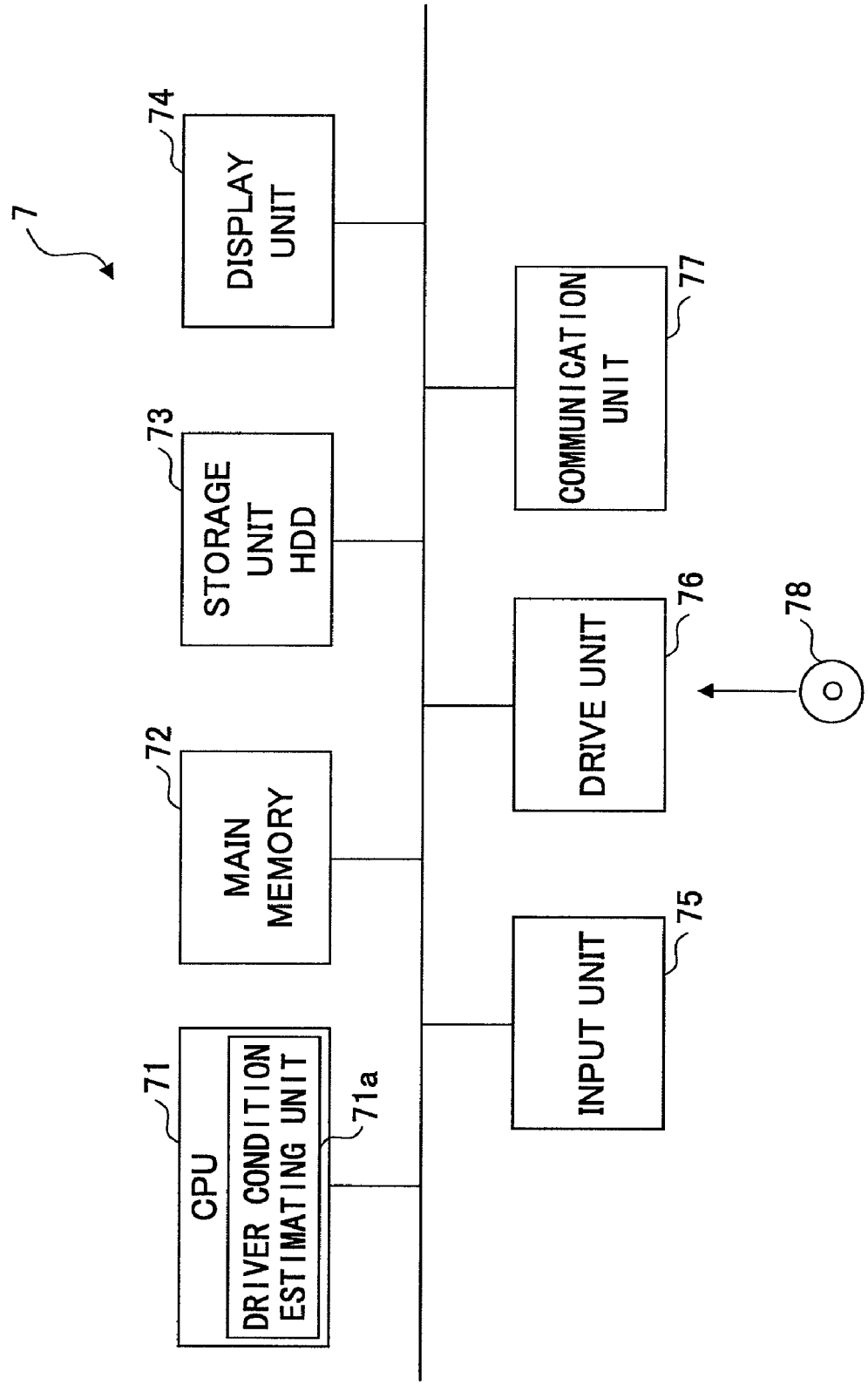
FIG. 5 is a block diagram illustrating an exemplary hardware configuration of a server.

FIG. 5 is a block diagram illustrating an exemplary hardware configuration of the server 7. The server 7 includes a CPU 71, a main memory 72, a storage unit 73 such as a hard disk drive (HDD), a display unit 74, an input unit 75, a drive unit 76, and a communication unit 77 that are connected to each other via a bus.

The CPU 71 implements various functions of the server 7 and controls various processes in the server 7 by loading programs such as an operating system and applications from the storage unit 73 and executing the loaded programs. The main memory 72 is implemented by, for example, a RAM and is used as a work area for temporarily storing programs and data. The storage unit 73 is implemented by a non-volatile memory such as an HDD or a flash memory and is used to store an operating system, programs, and drivers. The display unit 74 generates screens with resolutions and numbers of colors specified by programs, and displays the generated screens on a display such as a liquid crystal display. For example, the display unit 74 generates and displays graphical user interfaces (GUIs) including windows and data for user operations.

The input unit 75 includes, for example, a keyboard and a mouse, and is used to enter user instructions. The drive unit 76 accommodates a storage medium 78, reads data from the storage medium 78, and sends the read data to, for example, the main memory 72. The communication unit 77 is implemented by, for example, a modem or an NIC, and connects the server 7 to a network such as the Internet or a LAN.

A driver condition estimating unit 71a is implemented by executing a program by the CPU 71. The driver condition estimating unit 71a transfers the before-boarding behavior information from the information collecting device 60 to the vehicle 3, determines whether the driver is irritated based on the before-boarding behavior information as described later, and sends the determination result to the vehicle 3. If irritation information (indicating whether the driver is irritated) is sent from the information collecting device 60, the driver condition estimating unit 71a also transfers the irritation information to the vehicle 3. Thus, whether the driver is irritated may be determined by any one of the information collecting device 60, the server 7, and the vehicle 3.

[B. Behavior Indicating Irritation of Driver to be Detected when Driver Gets into Vehicle]

Behavior indicating irritation of the driver to be detected when the driver gets into the vehicle 3 is described below. If the driver is irritated when getting into the vehicle 3, the driver's action tends to become quicker. Therefore, it is possible to determine whether the driver is irritated by detecting the speed of various operations performed when the driver gets into the vehicle 3.

Figure 6:
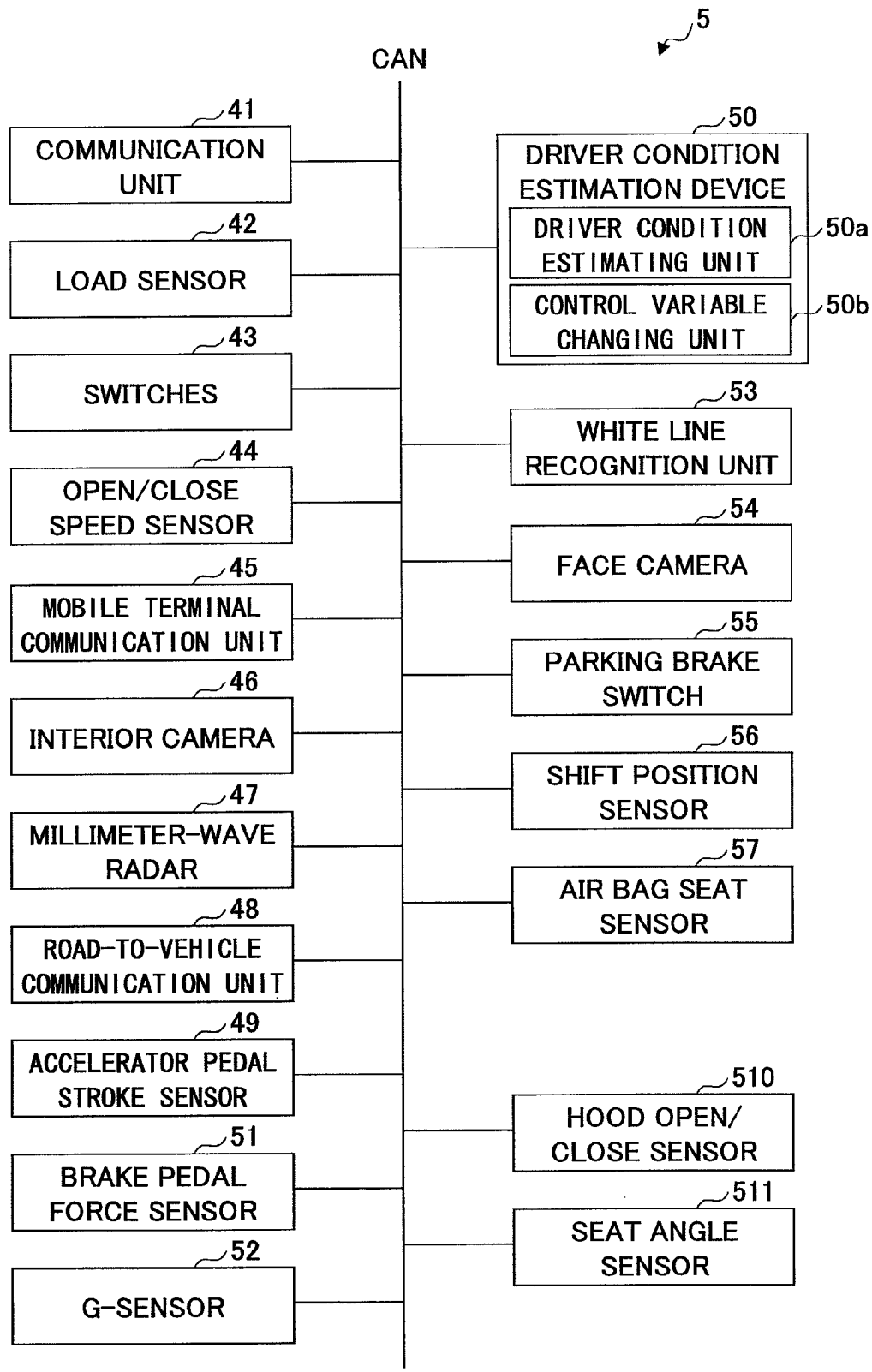
FIG. 6 is a block diagram illustrating an exemplary configuration of a driver condition estimation apparatus.

FIG. 6 is a block diagram illustrating an exemplary configuration of the driver condition estimation apparatus 5. The driver condition estimation apparatus 5 includes a driver condition estimation device 50 for controlling the operations of the driver condition estimation apparatus 5. The driver condition estimation device 50 collects during-boarding behavior information and in-vehicle behavior information of the driver from sensors and other devices and includes a driver condition estimating unit 50a for determining whether the driver is irritated. The driver condition estimation device 50 is a computer including a CPU and memories such as a ROM and a RAM and implements the driver condition estimating unit 50a by executing a program stored in a memory.

A communication unit 41 connects the driver condition estimation apparatus 5 to a network such as a cell-phone network, a PHS network, or a wireless LAN and receives before-boarding behavior information and irritation information from the information center 2. A load sensor 42 is, for example, implemented by piezoelectric elements disposed in the seats of the vehicle 3. The load sensor 42 detects whether the driver is in the vehicle 3 and the number of passengers. Switches 43 are buttons and switches of in-vehicle devices such as a car navigation system and an engine starter, and detect operational errors, redoes, and operating forces of the driver. An open/close speed sensor 44 detects the speed at which doors and a trunk lid are opened and closed and is implemented by sensors for detecting positional changes of hinges of the doors and the trunk lid. A mobile terminal communication unit 45 enables wireless or wired communications between, for example, a car navigation system and the mobile terminal 13 of the driver. For example, with Bluetooth technology, the mobile terminal communication unit 45 and the mobile terminal 13 automatically start communications when the driver gets into the vehicle 3. The mobile terminal communication unit 45 also enables hands-free conversation. A voice uttered by the driver is sent from the mobile terminal communication unit 45 to the mobile terminal 13, and a voice received by the mobile terminal 13 from the cell-phone network is sent to the mobile terminal communication unit 45 and is output from an in-vehicle speaker. Also, the mobile terminal communication unit 45 may be configured to cause the car navigation system to display or read out an email message received or transmitted by the mobile terminal 13. An interior camera 46 includes a photoelectric conversion element such as a charge coupled device (CCD) mounted on an instrument panel to face to the rear of the vehicle, and detects a moving object in the cabin. Movement of an object is detected, for example, based on variation of pixel values (e.g., luminance) of image data and the speed of the movement is determined based on the speed of variation of the pixel values.

A millimeter-wave radar 47 transmits a millimeter wave with a predetermined wavelength and determines the distance from an obstacle and the relative velocity based on the time taken by the millimeter wave to return from the obstacle and the frequency change of the millimeter wave. A road-to-vehicle communication unit 48 communicates with the base station 8 of, for example, a vehicle information and communication system (VICS) or a dedicated short range communication (DSRC) system provided on the roadside via a radio signal or a beacon. The road-to-vehicle communication unit 48 receives road congestion information and statuses of traffic lights from the base station 8. An accelerator pedal stroke sensor 49 detects the amount of depressing the accelerator pedal by the driver and detects an accelerator level based on the amount of depressing the accelerator pedal. A brake pedal force sensor 51 detects depression of the brake pedal by the driver and the force applied to the brake pedal. A G-sensor 52 detects acceleration and deceleration of the vehicle 3. A white line recognition unit 53 detects right and left white lines separating driving lanes based on image data of the road ahead taken by a camera. A face camera 54 is mounted, for example, on the steering column and obtains image data of the face of the driver. The face camera 54 processes the image data and detects the orientation of the face and detects whether the eyes of the driver are open or closed. A parking brake switch 55 detects the status of the parking brake. A shift position sensor 56 detects the current shift position (e.g., D, 1, 2, N, or R). An air bag seat sensor 57 detects whether passengers are seated and detects approximate heights of seated passengers. A hood open/close sensor 510 detects whether the hood is open. A seat angle sensor 511 detects the angle of the backrest of the driver's seat.

The driver condition estimating unit 50a detects behavior indicating irritation of the driver when the driver gets into the vehicle 3. For example, if the load sensor 42 momentarily detects a large load or the interior camera 46 detects movement of baggage, the driver condition estimating unit 50a determines that baggage has been thrown into the vehicle 3. If the open/close speed sensor 44 detects that a door or the trunk lid is opened or closed at a speed higher than or equal to a threshold, the driver condition estimating unit 50a determines that the door or the trunk lid has been opened or closed violently. If, for example, the switches 43 are operated repeatedly or with a strong force, or operations are redone several times, the driver condition estimating unit 50a determines that there have been switch operation errors or the switches 43 have been operated roughly. If the mobile terminal communication unit 45 detects that the mobile terminal 13 in the vehicle 3 is engaged on a call, the driver condition estimating unit 50a determines that the driver is talking on the mobile terminal 13. Also, if the time lag between when the door is opened and when the engine is started is short or the driver starts the engine without fastening the seat belt, the driver condition estimating unit 50a determines that the driver is irritated. Since the time lag between opening the door and starting the engine and the timing of fastening the seat belt vary from person to person, it is preferable to record past behavior of the driver and to determine whether the driver is irritated by comparing the current behavior of the driver with the past behavior.

Figure 7:
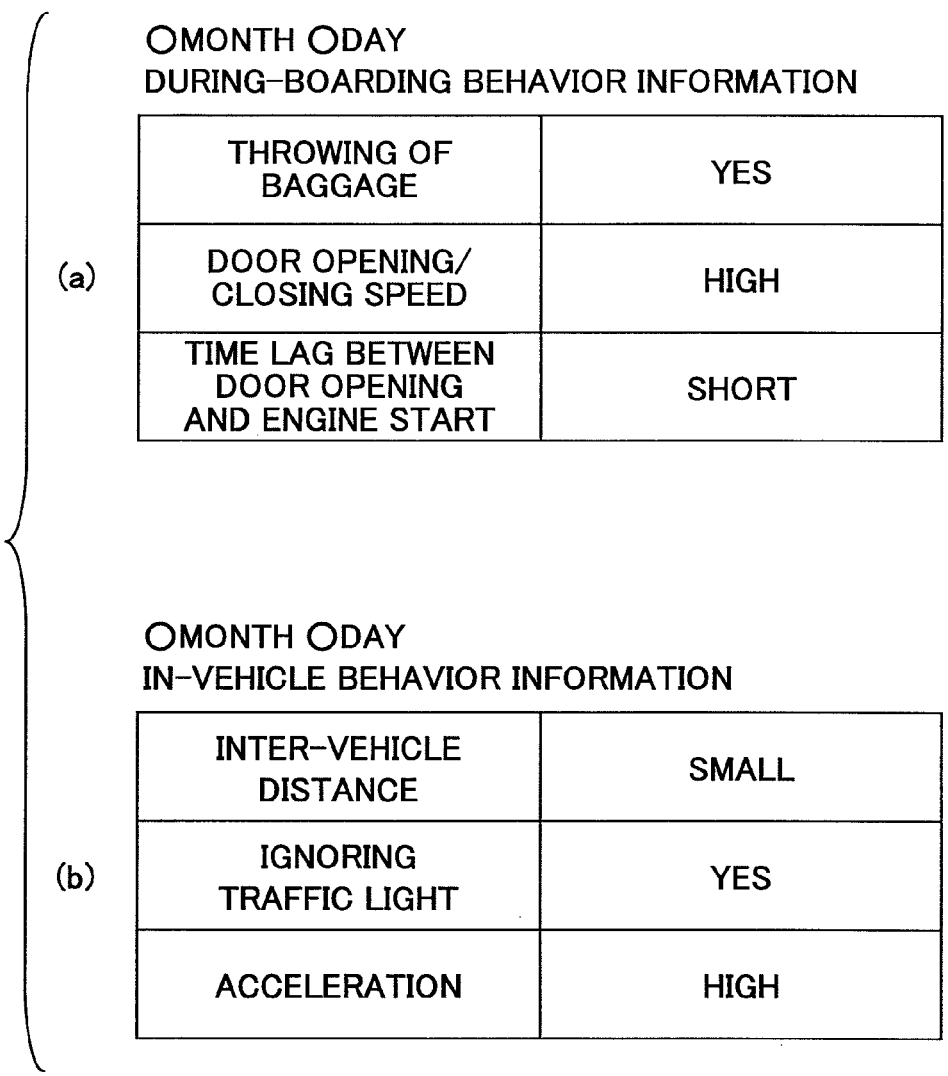
FIG. 7 is a table showing exemplary during-boarding behavior information and in-vehicle behavior information.

If behavioral events indicating irritation of the driver are detected, the driver condition estimating unit 50a records the behavioral events as during-boarding behavior information as exemplified in FIG. 7 (a). In FIG. 7 (a), the following behavioral events are recorded: "Throwing of baggage: yes", "Door opening/closing speed: high", and "Time lag between door opening and engine start: short". Here, it is assumed that as the number of detected behavioral events increases, the level of irritation of the driver increases. The during-boarding behavior information may instead be represented by a table listing all detectable behavioral events with flags that are turned on when the corresponding behavioral events are detected.

[C. Behavior Indicating Irritation of Driver to be Detected During Driving]

Behavior indicating irritation of the driver during driving is described below. The configuration of the driver condition estimation apparatus 5 is substantially the same as that shown in FIG. 6.

The driver condition estimating unit 50a detects behavior indicating irritation of the driver while the driver is driving. For example, if the distance from a vehicle ahead detected by the millimeter-wave radar 47 is small, the driver condition estimating unit 50a determines that the driver is irritated. The driver condition estimating unit 50a obtains the status of a traffic light from, for example, the road-to-vehicle communication unit 48 or based on a front view image taken by a camera, and determines that the driver is irritated if the vehicle 3 passes through the intersection when the traffic light is yellow. If the accelerator level detected by the accelerator pedal stroke sensor 49 is greater than a threshold or the acceleration detected by the G-sensor 52 is greater than a threshold, the driver condition estimating unit 50a determines that the driver is irritated. If the braking timing detected by the brake pedal force sensor 51 is late relative to the distance from a vehicle ahead detected by the millimeter-wave radar 47 or the deceleration detected by the G-sensor 52 is greater than a threshold, the driver condition estimating unit 50a determines that the driver is irritated. The white line recognition unit 53 detects the vehicle 3 when it crosses a white line and thereby detects changing of driving lanes. If the frequency of changing driving lanes is greater than or equal to a threshold, the driver condition estimating unit 50a determines that the driver is irritated. Also, if zigzag movement of the vehicle 3 with respect to a white line is detected, the driver condition estimating unit 50a determines that the driver is irritated. Further, if the vehicle 3 is in the fast lane (for example, the right-most lane) of an expressway longer than or equal to a predetermined period of time, the driver condition estimating unit 50a determines that the driver is irritated. If the driver's face or the driver's eyes are fixed in the forward direction or frequently change directions, the driver condition estimating unit 50a determines that the driver is irritated. If the parking brake switch 55 is turned on even during driving, the driver condition estimating unit 50a determines that the driver is irritated. If continuous driving time (measured from when the engine is started) becomes greater than or equal to a threshold, the driver condition estimating unit 50a determines that the driver is so irritated as not to take a rest.

If voices (indicating, for example, a yell, a call of nature, sickness, and a cry) that may make the driver irritated are detected by a microphone and a voice recognition device in conversations of passengers in a moving vehicle, the driver condition estimating unit 50a determines that the driver is irritated. Also, the driver condition estimating unit 50a may be configured to determine that the driver is irritated if a traffic jam is detected based on information from the VICS or if it becomes difficult to increase the speed because of rainy or foggy weather.

If behavioral events indicating irritation of the driver are detected, the driver condition estimating unit 50a records the behavioral events as in-vehicle behavior information as exemplified in FIG. 7 (b). In FIG. 7 (b), the following behavioral events are recorded: "Inter-vehicle distance: small", "Ignoring traffic light: yes", and "Acceleration: high". Here, it is assumed that as the number of detected behavioral events increases, the level of irritation of the driver increases. The in-vehicle behavior information may instead be represented by a table listing all detectable behavioral events with flags that are turned on when the corresponding behavioral events are detected.

[Process of Determining Whether Driver is Irritated]

An exemplary process, by the driver condition estimating unit 50a, of determining whether the driver is irritated is described below. The driver condition estimating unit 50a obtains the before-boarding behavior information and the during-boarding information, for example, before the engine is started, and also obtains the in-vehicle behavior information during driving. Here, as described above, it is assumed that as the number of detected behavioral events in the before-boarding, during-boarding, and in-vehicle behavior information increases, the level of irritation of the driver increases. For example, the driver condition estimating unit 50a determines that the driver is irritated if the number of detected behavioral events is greater than or equal to a threshold and determines the level of irritation according to the number of detected behavioral events.

Figure 8:
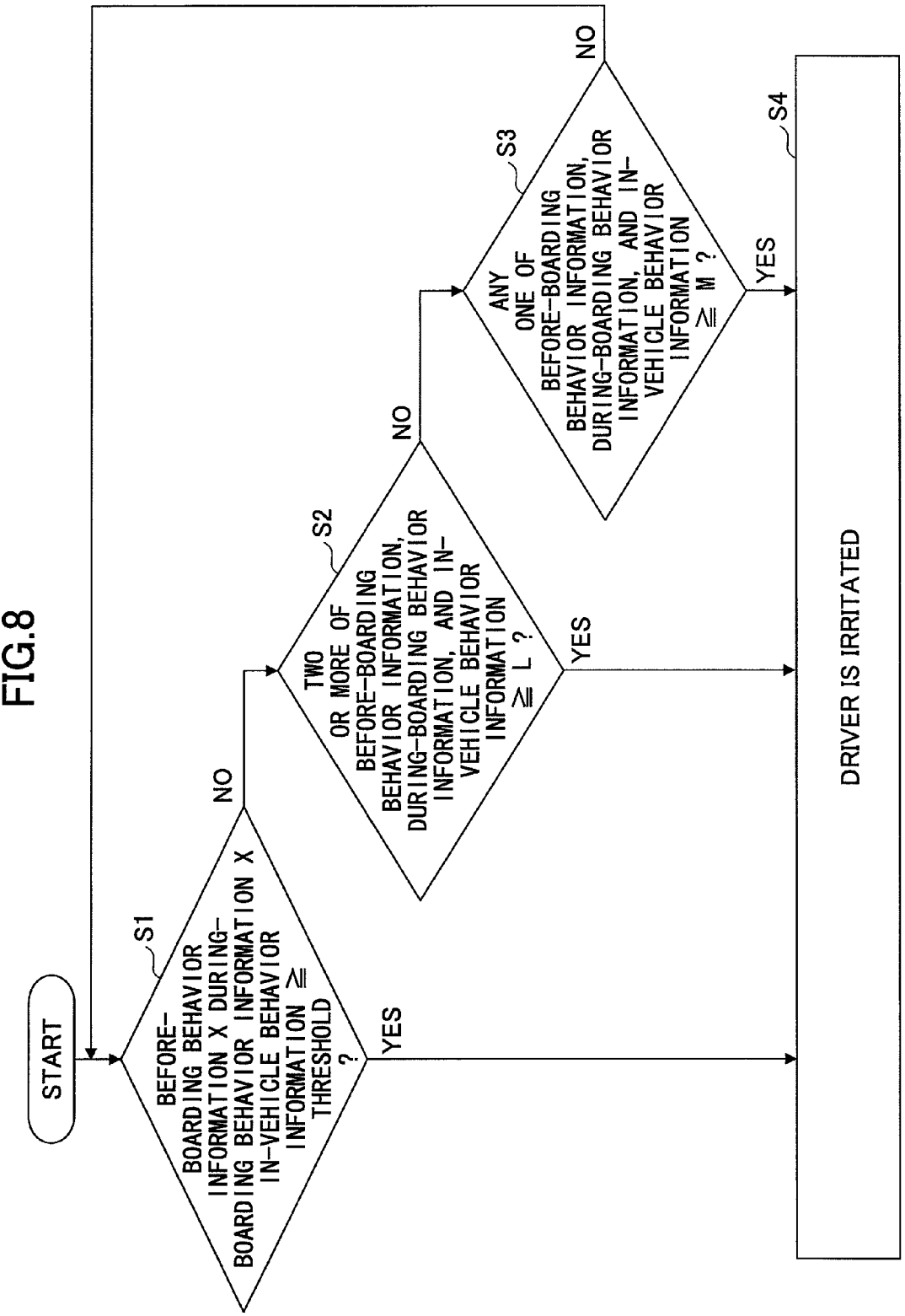
FIG. 8 is a flowchart showing a process of determining whether a driver is irritated.

FIG. 8 is a flowchart showing a process of determining whether the driver is irritated. The driver condition estimating unit 50a multiplies the numbers of detected behavioral events in the before-boarding behavior information, the during-boarding behavior information, and the in-vehicle behavior information. If the result of multiplication is greater than or equal to a threshold (YES in S1), the driver condition estimating unit 50a determines that the driver is irritated (S4). If the result of multiplication is less than the threshold (NO in S1), the driver condition estimating unit 50a determines whether two or more of the numbers of detected behavioral events in the before-boarding behavior information, the during-boarding behavior information, and the in-vehicle behavior information are greater than or equal to a predetermined value L (S2). If two or more of the numbers of detected behavioral events are greater than or equal to the value L (YES in S2), the driver condition estimating unit 50a determines that the driver is irritated (S4). If less than two of the numbers of detected behavioral events are greater than or equal to the value L (NO in S2), the driver condition estimating unit 50a determines whether any one of the numbers of detected behavioral events in the before-boarding behavior information, the during-boarding behavior information, and the in-vehicle behavior information is greater than or equal to a predetermined value M (M>L) (S3). If any one of the numbers of detected behavioral events is greater than or equal to the value M (YES in S3), the driver condition estimating unit 50a determines that the driver is irritated (S4) If the driver is not determined to be irritated until the driver gets into the vehicle 3, the driver condition estimating unit 50a repeatedly determines whether the driver is irritated based on the in-vehicle behavior information.

The level of irritation may be determined at multiple stages based on a value obtained by multiplying the numbers of detected behavioral events in the before-boarding behavior information, the during-boarding behavior information, and the in-vehicle behavior information or on the sum of the numbers of detected behavioral events.

It is not necessary to use all of the before-boarding behavior information, the during-boarding behavior information, and the in-vehicle behavior information to determine whether the driver is irritated. Whether the driver is irritated may be determined based on any one of or any combination of the before-boarding behavior information, the during-boarding behavior information, and the in-vehicle behavior information.

Meanwhile, whether the driver becomes irritated and the level of irritation may vary depending on age, sex, environment, and so on. Therefore, the driver condition estimation apparatus 5 is preferably configured to obtain information such as age, sex, and environment and to determine whether the driver is irritated using the obtained information as weighting coefficients. The age and sex of the driver may be pre-registered in the information center 2 or the vehicle 3, or may be read by a card reader from an IC-card driver's license. Environmental information such as rain, snow, and traffic jam may be obtained from a rain sensor and the VICS. When determining whether the driver is irritated, the driver condition estimating unit 50a multiplies the numbers of behavioral events or the values M and L by weighting coefficients corresponding to the age, sex, and environment. For example, it is considered that irritation is more likely to affect driving as the driver gets older. Therefore, weighting coefficients for age are preferably determined such that the probability of an elderly person being determined to be irritated increases. Weighting coefficients for sex are preferably determined such that probability of men being determined to be irritated increases. Also, weighting coefficients for environment are preferably determined such that probability of the driver being determined to be irritated increases when the weather is rainy or the road is congested.

[Vehicle Characteristics when Driver is Determined to be Irritated]

Vehicle controls performed when the driver is determined to be irritated are described below. When irritated, the driver tends to drive the vehicle at high speed and as a result, the amount of exhaust gas may increase. Therefore, when the driver is irritated, it is preferable to warn the driver and to control the vehicle to prevent over-speeding.

Figure 9:
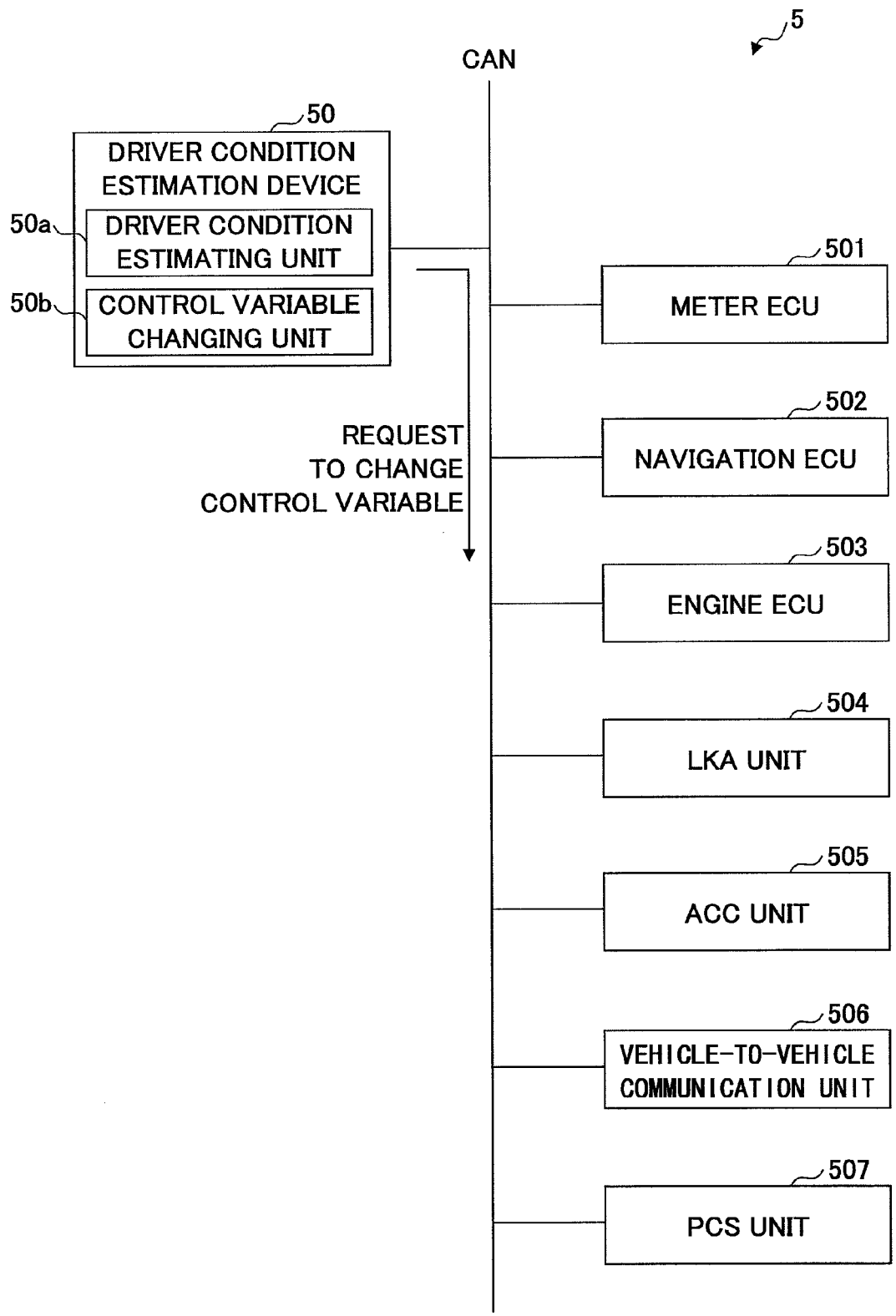
FIG. 9 is a block diagram illustrating a control system for controlling a vehicle when a driver is determined to be irritated.

FIG. 9 is a block diagram illustrating a control system of the vehicle 3 for controlling the vehicle 3 when the driver is determined to be irritated. The driver condition estimation device 50 is connected via an in-vehicle LAN such as a controller area network (CAN) to a meter ECU 501, a navigation ECU 502, an engine ECU 503, a lane keeping assist (LKA) unit 504, an adaptive cruise control (ACC) unit 505, and a vehicle-to-vehicle communication unit 506. If the driver condition estimating unit 50a determines that the driver is irritated, a control variable changing unit 50b of the driver condition estimation device 50 requests the ECUs to change control variables.

Vehicle controls to be performed when the driver is determined to be irritated include safety controls and an environmental control, and the safety controls are classified into three categories.

Safety Control I: Caution and Warning for Driver

The meter ECU 501 turns on lamps on a combination panel and outputs a waning sound. For example, in response to a request from the control variable changing unit 50b, the meter ECU 501 displays information for calming down the driver when the ignition is turned on. More preferably, the navigation ECU 502 for controlling a navigation system is used to display the information for calming down the driver. With the navigation ECU 502, it is possible to provide the information in various manners. Examples of information for calming down the driver include a message such as "You are irritated. Please drive safely", a graph showing a relationship between the level of irritation and the degree of risk with the current level of irritation highlighted, and a family picture. Also, it is possible to output a pre-recorded voice message of the driver or a family member (e.g., "Be cool and drive carefully") or a classical music from a speaker.

Safety Control II: Changing Vehicle Control Variables by Autonomous System

The engine ECU 503 determines target torque and then an engine control level by referring to an acceleration map based on the accelerator level, and also controls the transmission by referring to a shift map to achieve target acceleration. When irritation of the driver is detected and a request is sent from the control variable changing unit 50b, the engine ECU 503 determines the engine control level and controls the gear shifter to make the acceleration and speed of the vehicle 3 lower than normal.

The LKA unit 504 outputs a warning sound if the deviation from a target traveling line, which is substantially in the middle between right and left white lines, exceeds a threshold. When irritation of the driver is detected and a request is sent from the control variable changing unit 50b, the LKA unit 504 decreases the threshold.

The ACC unit 505 causes the vehicle 3 to follow a vehicle ahead at a distance selected, for example, from three levels. When irritation of the driver is detected and a request is sent from the control variable changing unit 50b, the ACC unit 505 sets the distance at the highest one of the three levels or at an even higher level. The above measures allow the driver to notice that he/she is irritated and to calm down. Also, outputting a warning sound at an earlier timing and setting the inter-vehicle distance at a higher level make it possible to ensure the safety even when the driver is irritated. Also, when requested by the control variable changing unit 50b, a pre-crash safety system (PCS) 507 sets the threshold of the time to collision (TTC) for outputting a warning sound longer than normal.

Meanwhile, the above safety measures may be bothersome for a driver. Therefore, the control variable changing unit 50b may be configured to perform controls as described above after reporting to the driver. If the LKA unit 504 and the ACC unit 505 are turned off by the driver, the control variable changing unit 50*b* turns on the units after reporting and then starts the safety control.

Safety Control III: Vehicle Control by Autonomous and Infrastructure Systems

The vehicle-to-vehicle communication unit 506 includes a transceiver and communicates with other vehicles by sending and receiving radio frequency waves (for example, millimeter waves in a frequency band between 300 Hz and 30 GHZ) via a communication antenna. For example, when the level of irritation is fairly high and a request is sent from the control variable changing unit 50*b*, the vehicle-to-vehicle communication unit 506 warns other vehicles around the vehicle 3 or requests other vehicles to take evasive action to secure safety. The control variable changing unit 50*b* may be configured to take into account the vehicle behavior (speed, zigzag movement, inter-vehicle distance, etc.) in addition to the level of irritation to determine the level of danger and to request other vehicles to take evasive action.

Environmental Control Controlling Vehicle in Environmentally-Friendly Manner

As in "Safety Control II", the engine ECU 503 determines the engine control level and controls the gear shifter to make the acceleration and speed of the vehicle 3 lower than normal, and thereby controls the vehicle 3 in an environmentally-friendly manner. If the vehicle 3 is a hybrid vehicle or an electric vehicle where power is generated by regenerative braking, the engine ECU 503 causes the vehicle 3 to frequently enter the regenerative mode and to reduce the vehicle speed, and thereby controls the vehicle 3 in an environmentally-friendly manner.

[Process of Determining Whether Driver has Calmed Down]

Irritation of the driver is not permanent. Therefore, it is preferable to end the safety and environmental controls when the driver has calmed down. The driver condition estimating unit 50*a* detects behavior of the driver when the driver gets into the vehicle 3 and during driving, and determines that the driver has calmed down if a behavioral event indicating that the driver is in a normal mental condition (not irritated) is detected. As shown in FIG. 6, the driver condition estimation apparatus 5 of the vehicle 3 includes the hood open/close sensor 510 and the seat angle sensor 511.

For example, it is generally recommended to open the hood and check the amounts of brake fluid and battery fluid before driving. If the driver performs such checking before driving, it can be assumed that the driver is not irritated or the level of irritation is low even if before-boarding behavior information is detected. Similarly, if the driver adjusts the angle of the seat before driving, it can be assumed that the driver is not irritated or the level of irritation is low. When opening and closing of the hood is detected by the hood open/close sensor 510 or adjustment of the seat is detected by the seat angle sensor 511, the driver condition estimating unit 50*a* records the detected event as calm behavior information.

During driving, it can be assumed that the driver is not irritated or the level of irritation is low if the driver allows a vehicle to get into a position in front of the vehicle 3, keeps driving in the same driving lane, keeps a fairly large distance from a vehicle ahead, or abides by stop signs. The driver condition estimating unit 50*a* records, for example, the following events as calm behavior information: the millimeter-wave radar 47 or the white line recognition unit 53 detects a vehicle getting into a position in front of the vehicle 3; the white line recognition unit 53 detects that the driver is driving on the same driving lane for a predetermined period of time; the distance from a vehicle ahead detected by the millimeter-wave radar 47 is greater than a predetermined value; and the vehicle 3 stops at stop signs detected by the navigation system or the road-to-vehicle communication unit 48.

The driver condition estimating unit 50*a* subtracts the number of behavioral events P in the calm behavior information from the sum of the numbers of behavioral events Q in the before-boarding behavior information, the during-boarding behavior information, and the in-vehicle behavior information, and ends the vehicle controls when the result of subtraction becomes a predetermined value. For example, the driver condition estimating unit 50*a* ends the vehicle controls when Q-P becomes 0.

Also, the driver condition estimating unit 50*a* may be configured to gradually end the vehicle controls. As described above, safety controls are categorized into Safety Control I, Safety Control II, and Safety Control III, and the intervention level of Safety Control I, Safety Control II, and Safety Control III increases in the order mentioned. The driver condition estimating unit 50*a* is preferably configured to decrease the intervention level as the number of behavioral events in the calm behavior information increases. For example, the driver condition estimating unit 50*a* ends Safety Control III when a behavioral event indicating calmness of the driver is detected, ends Safety Control II when another behavioral event indicating calmness is detected, and ends Safety Control I when still another behavioral event indicating calmness is detected. This approach makes it possible to gradually end the vehicle controls according to the level of irritation and thereby to effectively secure the safety.

[Process of Driver Condition Estimation Apparatus 5]

Figure 10:
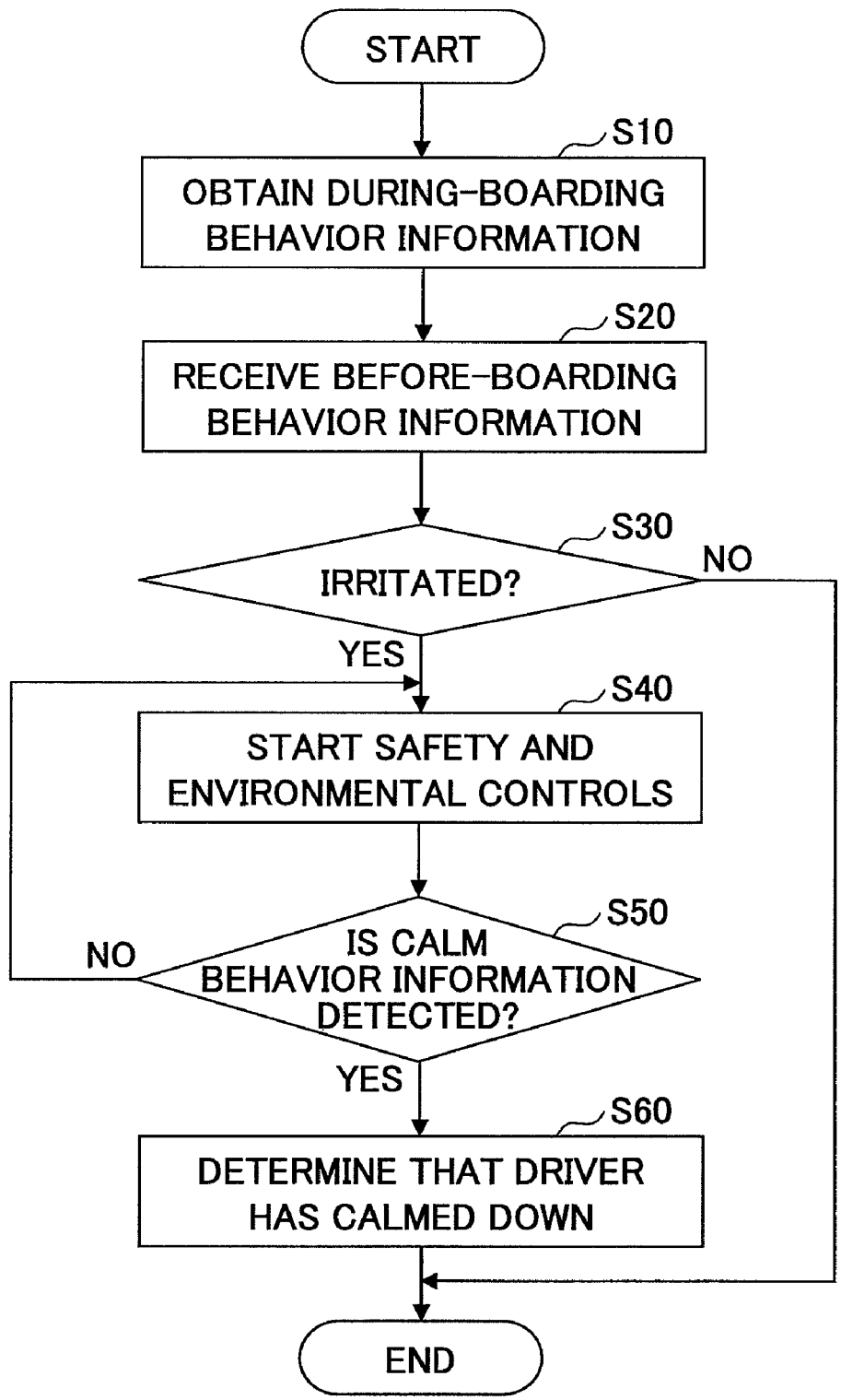
FIG. 10 is a flowchart showing a process performed by a driver condition estimation apparatus.

FIG. 10 is a flowchart showing a process performed by the driver condition estimation apparatus 5. The process shown in FIG. 10 is started, for example, when the door of the vehicle 3 is unlocked with a smart key.

When the door is unlocked, i.e., when the driver comes close to the vehicle 3, the driver condition estimating unit 50*a* obtains during-boarding behavior information (S10).

When the ignition is turned on, the driver condition estimating unit 50*a* receives before-boarding behavior information via the information center 2 (S20). Alternatively, the driver condition estimating unit 50*a* may be configured to receive the before-boarding behavior information before the driver reaches the vehicle 3 and the ignition is turned on.

Then, the driver condition estimating unit 50*a* determines whether the driver is irritated based on the numbers of detected behavioral events in the before-boarding behavior information and the during-boarding behavior information (S30). For example, the driver condition estimating unit 50*a* determines that the driver is irritated if the result of multiplying the numbers of detected behavioral events in the before-boarding behavior information and the during-boarding behavior information is greater than or equal to a threshold, or either one of the numbers of detected behavioral events is greater than or equal to a threshold.

If the driver is not irritated (NO in S30), the driver condition estimating unit 50*a* terminates the process. If the driver is irritated (YES in S30), the driver condition estimating unit 50*a* starts the safety controls I-III and the environmental control (S40).

While the vehicle 3 is running, the driver condition estimating unit 50*a* determines whether calm behavior information is detected (S50). For example, if the number of detected behavioral events indicating calmness of the driver becomes greater than or equal to a threshold, the driver condition estimating unit 50*a* determines that the calm behavior information is detected.

If the calm behavior information is detected (YES in S50), the driver condition estimating unit 50a determines that the driver has calmed down and ends the safety controls and the environmental control (S60).

Figure 11:
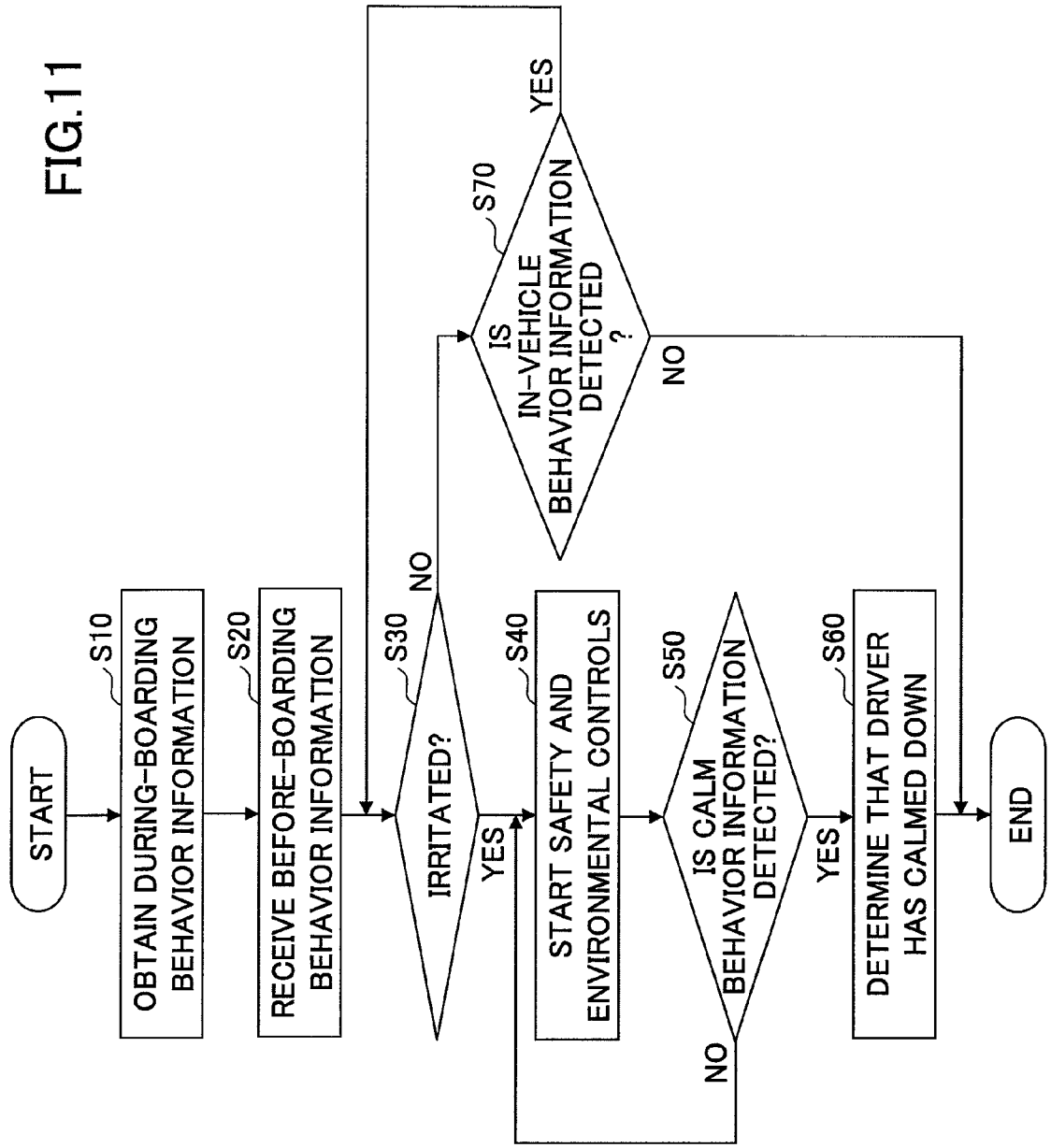
FIG. 11 is another flowchart showing a process performed by a driver condition estimation apparatus.

FIG. 11 is another flowchart showing a process performed by the driver condition estimation apparatus 5. In the flowchart shown in FIG. 11, in-vehicle behavior information is also taken into account to determine whether to perform the safety controls and the environmental control. In FIG. 11, the same reference numbers are used for steps corresponding to those in FIG. 10.

When the door is unlocked, i.e., when the driver comes close to the vehicle 3, the driver condition estimating unit 50a obtains during-boarding behavior information (S10).

When the ignition is turned on, the vehicle 3 receives before-boarding behavior information via the information center 2 (S20). Alternatively, the vehicle 3 may be configured to receive the before-boarding behavior information before the driver reaches the vehicle 3 and the ignition is turned on.

Then, the driver condition estimating unit 50a determines whether the driver is irritated based on the numbers of behavioral events in the before-boarding behavior information and the during-boarding behavior information (S30). For example, the driver condition estimating unit 50a determines that the driver is irritated if the result of multiplying the numbers of behavioral events in the before-boarding behavior information and the during-boarding behavior information is greater than or equal to a threshold, or either one of the numbers of behavioral events is greater than or equal to a threshold.

If the driver is not irritated (NO in S30), the driver condition estimating unit 50a does not perform any control while the driver is getting into the vehicle 3, and continues to determine whether in-vehicle behavior information is detected during driving (S70). If the number of behavioral events detected during driving becomes greater than or equal to a threshold, the driver condition estimating unit 50a determines that the in-vehicle behavior information is detected and proceeds to step S30.

If the driver is irritated (YES in S30), the driver condition estimating unit 50a starts the safety controls I-III and the environmental control (S40).

While the vehicle 3 is running, the driver condition estimating unit 50a determines whether calm behavior information is detected (S50). For example, if the number of detected behavioral events indicating calmness of the driver becomes greater than or equal to a threshold, the driver condition estimating unit 50a determines that the calm behavior information is detected.

If the calm behavior information is detected (YES in S50), the driver condition estimating unit 50a ends the safety controls and the environmental control (S60).

Thus, this embodiment makes it possible to detect irritation of the driver when the driver is at home and getting into a vehicle, and to start controlling the vehicle in a safe and environmentally-friendly manner even before the driver starts driving. In other words, this embodiment makes it possible to determine whether the driver is irritated at an early stage and to control a vehicle in a safe and environmentally-friendly manner.

Second Embodiment

In the first embodiment, whether the driver is irritated is determined based on the behavior of the driver when the driver is at the home 1, getting into the vehicle 3, and in the vehicle 3. However, the determination result based on the driver's behavior is not always accurate. Therefore, in this embodiment, factors that more directly cause irritation of the driver are detected. For example, events such as a sudden family bereavement, childbearing by the wife, and a traffic accident of a family member may happen to anyone and are very likely to cause irritation for the driver. Therefore, it is possible to accurately determine whether the driver is irritated by detecting such events in addition to the behavior of the driver. Events causing irritation of the driver may be detected, for example, from a schedule, an email message, a conversation, and a telephone conversation.

[Before Getting into Vehicle]

Figure 12:
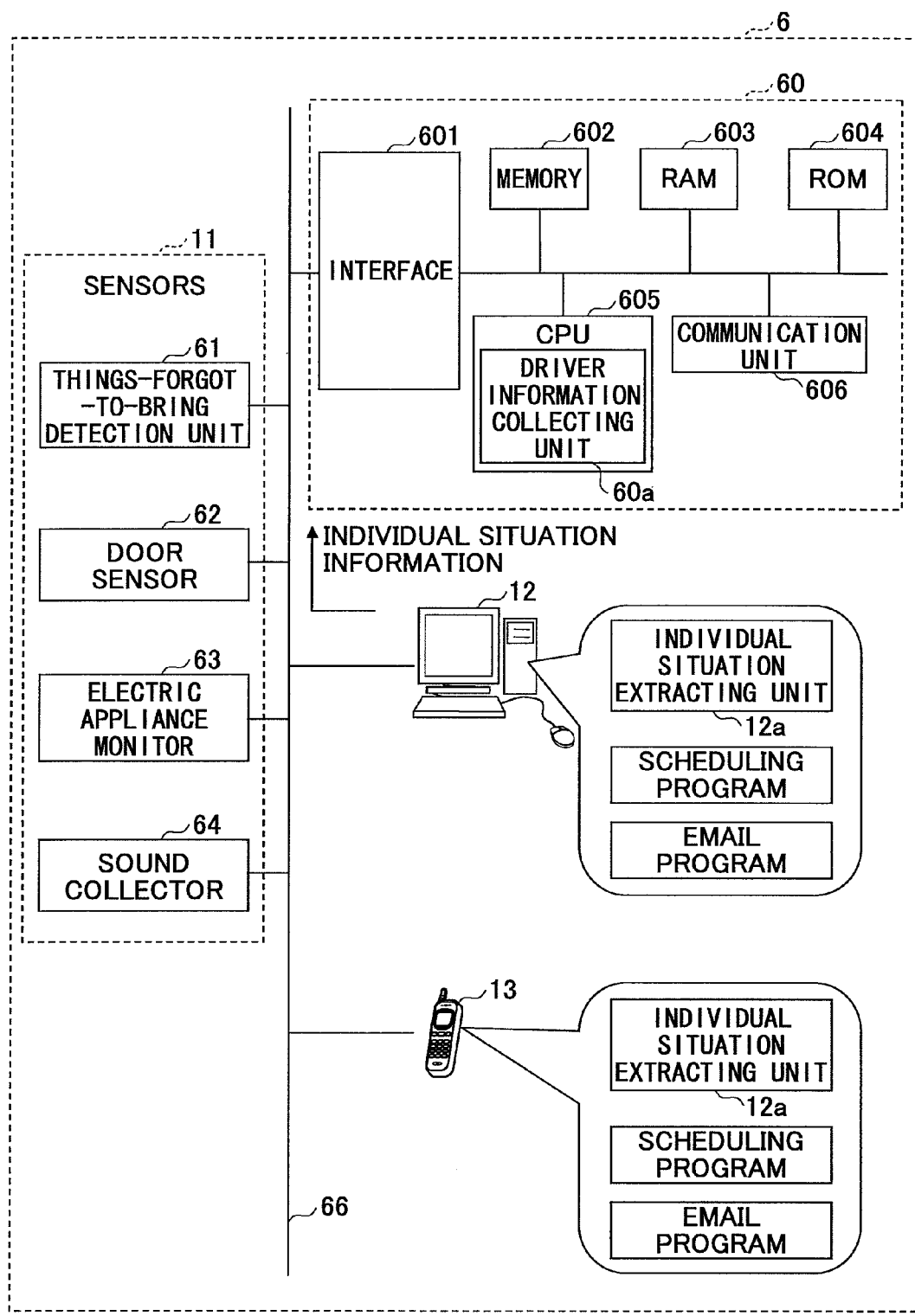
FIG. 12 is a block diagram illustrating an exemplary configuration of a driver information collecting apparatus according to a second embodiment.

FIG. 12 is a block diagram illustrating a configuration of the driver information collecting apparatus 6 according to the second embodiment. In FIG. 12, the same reference numbers are used for parts corresponding to those shown in FIG. 3, and descriptions of those parts are omitted. As shown in FIG. 12, the information collecting device 60 is connected via a network such as a LAN to a personal computer (PC) 12.

The PC 12 includes a CPU, a ROM, a RAM, and an HDD and executes a scheduling program and an email program stored in the HDD. The driver manages schedules and sends and receives email messages using the scheduling program and the email program. Also, the PC 12 executes a program stored in the HDD to implement an individual situation extracting unit 12a for extracting individual situation information from schedules and email messages of the driver. The individual situation extracting unit 12a is a resident program and runs in the background while the scheduling program and the email program are running. Keywords (such as died, rush, right away, born, cry, funeral, wake, manager, executive officer, important, and presentation which can be added by the driver) are registered in the individual situation extracting unit 12a. The individual situation extracting unit 12a extracts such keywords from schedules and email messages and sends them as the individual situation information to the information collecting device 60.

Figure 13:
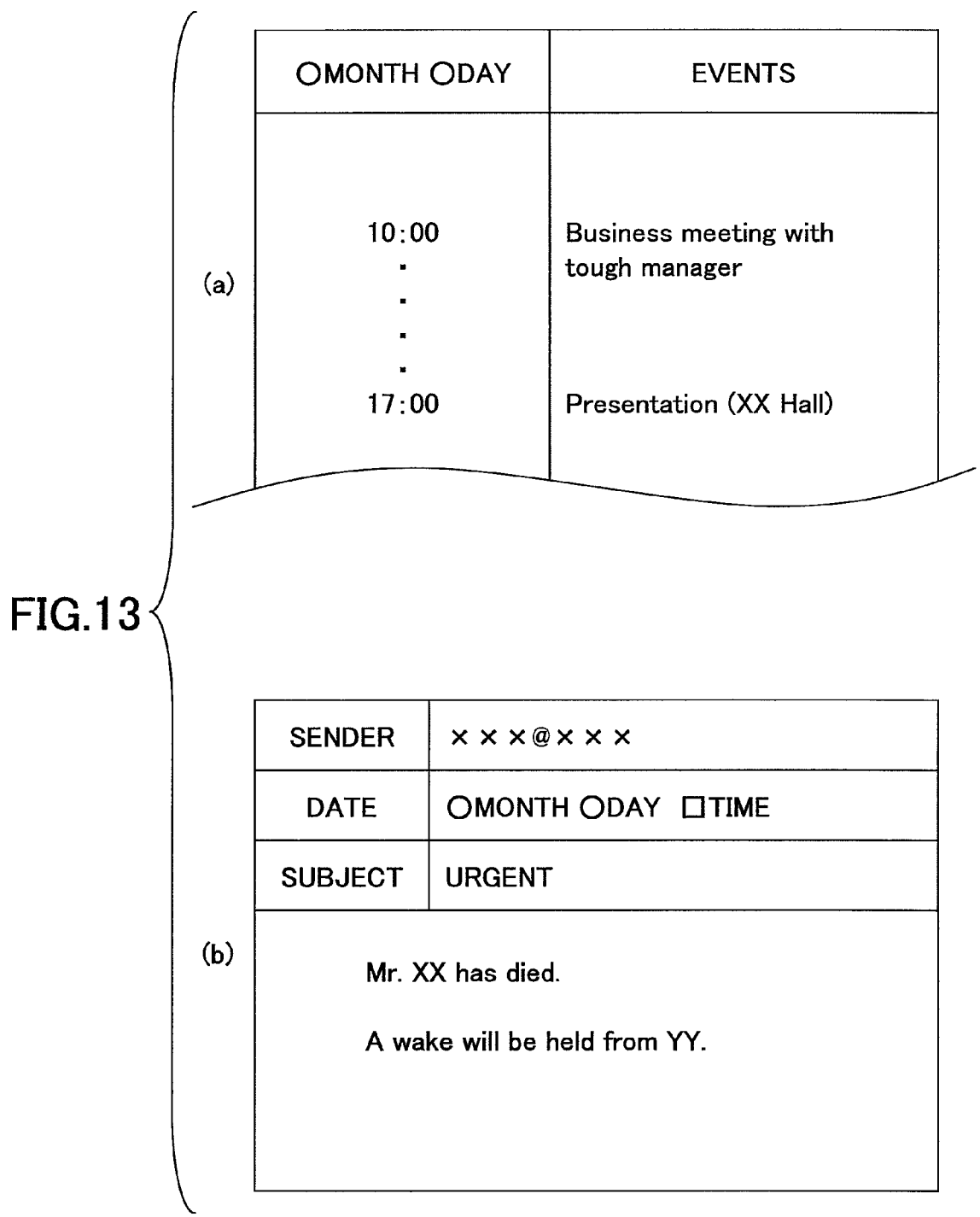
FIG. 13 is a drawing illustrating an exemplary schedule displayed by a scheduling program and an exemplary email message received by an email program.

FIG. 13 (a) shows an exemplary schedule displayed by the scheduling program and FIG. 13 (b) shows an exemplary email message received by the email program. The displayed schedule includes two scheduled events: "10:00 Business meeting with tough manager" and "17:00 Presentation (XX Hall)". The displayed email message includes text "Mr. XX has died. A wake will be held from YY." The individual situation extracting unit 12a extracts words "manager", "presentation", "died", and "wake" that correspond to the keywords from the schedule and the email message and sends the extracted words themselves or the number of the extracted words as individual situation information to the information collecting device 60.

The scheduling program and the email program may also be provided in the mobile terminal 13. The mobile terminal 13 is a computer including a CPU, a ROM, a RAM, a flash memory, and a transceiver for wirelessly sending and receiving email messages, and may be implemented, for example, as a cell phone, a personal data assistant, or a portable game device. Similar to the PC 12, the mobile terminal 13 includes a individual situation extracting unit 12a and sends individual situation information extracted from schedules and email messages to the information collecting device 60, for example, as an email message. As described later, the vehicle 3 receives the individual situation information extracted from schedules and email messages from the mobile terminal 13 when the mobile terminal 13 is brought into the vehicle 3. Meanwhile, the mobile terminal 13 and the PC 12 can synchronize schedules and email messages with each other. Therefore, the PC 12 may be configured to extract individual situation information from schedules and email messages of the mobile terminal 13 after synchronization.

Also, the information collecting device 60 extracts keywords from conversations between the driver and family members at the home 1 using the voice recognition function of the sound collector 64 and thereby accurately detects irritating situations.

The driver information collecting unit 60a sends the individual situation information via the information center 2 to the vehicle 3 each time when the individual situation information is detected or at regular intervals.

[When Getting into Vehicle/During Driving]

As described above, the vehicle 3 includes the mobile terminal communication unit 45. For example, the driver condition estimating unit 50a may be configured to extract keywords representing individual situation information from email messages sent to the mobile terminal 13 while the mobile terminal communication unit 45 is communicating with the mobile terminal 13. Meanwhile, when the driver is making a hands-free conversation, the sound of the conversation goes through, for example, a navigation system of the vehicle 3. Therefore, it is possible to extract keywords from the conversation by voice recognition. Also, it is possible to extract keywords from a conversation using a voice recognition device provided in the vehicle 3 to control in-vehicle devices. The driver condition estimating unit 50a stores keywords detected as described above when the driver gets into the vehicle 3 or during driving as individual situation information.

During driving, the driver may also be irritated by accidental events other than those detectable from email messages and schedules. For example, when the vehicle 3 hits an animal or a vehicle, it is highly likely that the driver becomes irritated. Also, when a police car or an ambulance approaches and the driver is requested to pull aside, the driver may be irritated. The driver condition estimation apparatus 5, for example, detects a collision of the vehicle 3 with an animal or a vehicle with a load sensor for inflating an air bag or based on an impact sound, detects the approach of a police car or an ambulance based on a sound of the siren, and records those events as individual situation information.

[Process of Determining Whether Driver is Irritated]

The driver condition estimating unit 50a receives individual situation information from the home 1 and also obtains individual situation information while the driver is in the vehicle 3. The individual situation information fairly accurately indicates irritation of the driver and is preferably given greater importance than the before-boarding, during-boarding, and in-vehicle behavior information in determining the irritation of the driver.

Figure 14:
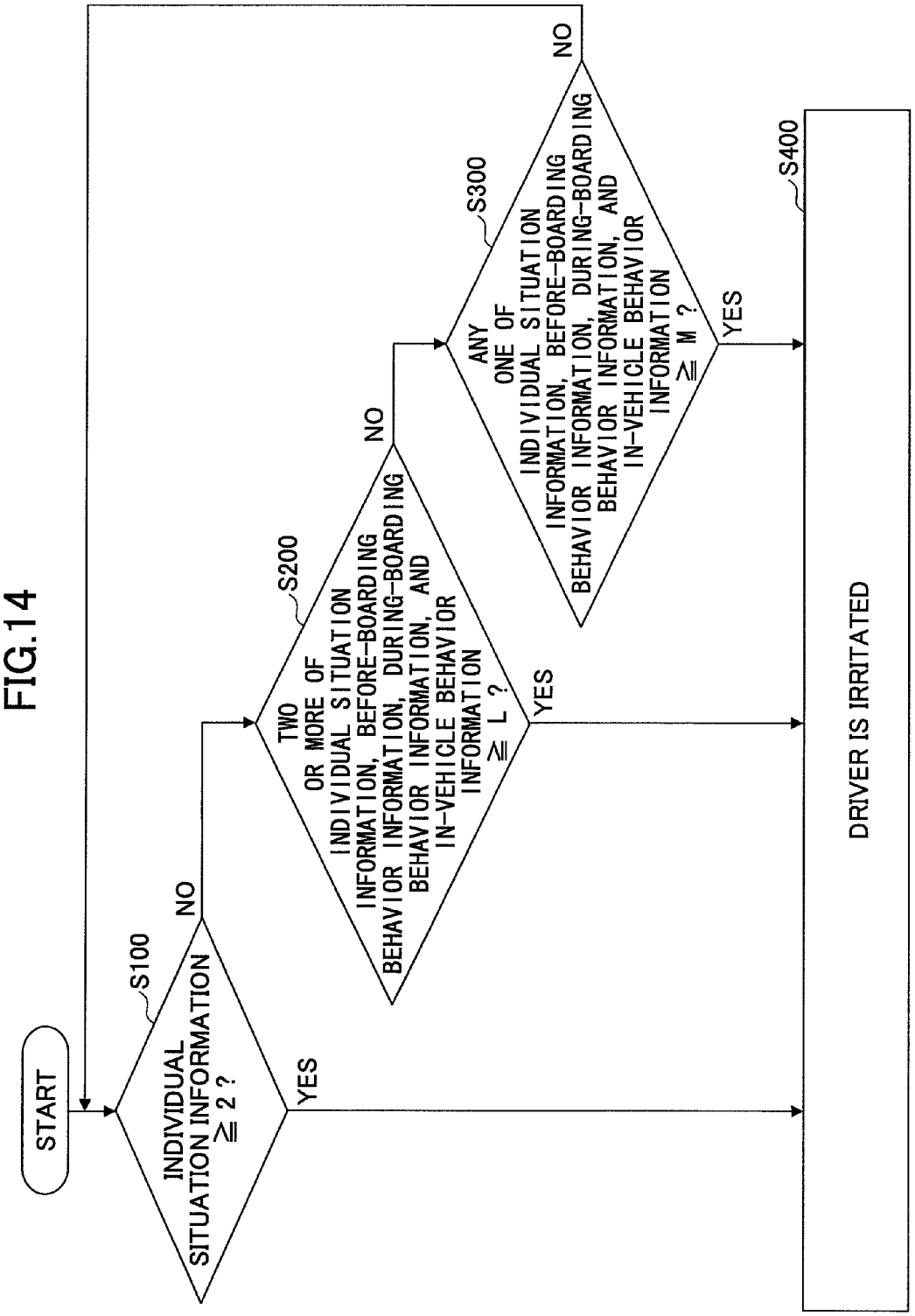
FIG. 14 is a flowchart showing a process of determining whether a driver is irritated according to the second embodiment.

FIG. 14 is a flowchart showing a process of determining whether the driver is irritated. The driver condition estimating unit 50a determines whether two or more individual situations (keywords) are detected as the individual situation information (S100). If the number of detected individual situations is greater than or equal to two (YES in S100), the driver condition estimating unit 50a determines that the driver is irritated (S400).

If the number of detected individual situations is less than two (NO in S100), the driver condition estimating unit 50a determines whether two or more of the numbers of detected situations or events in the individual situation information, the before-boarding behavior information, the during-boarding behavior information, and the in-vehicle behavior information are greater than a predetermined value L (S200). If two or more of the numbers of detected situations or events are greater than or equal to the value L (YES in S200), the driver condition estimating unit 50a determines that the driver is irritated (S400).

If less than two of the numbers of detected situations or events are greater than or equal to the value L (NO in S200), the driver condition estimating unit 50a determines whether any one of the numbers of detected situations or events in the individual situation information, the before-boarding behavior information, the during-boarding behavior information, and the in-vehicle behavior information is greater than or equal to a predetermined value M (M>L) (S300). If any one of the numbers of detected situations or events is greater than or equal to the value M (YES in S300), the driver condition estimating unit 50a determines that the driver is irritated (S400). As in the first embodiment, weighting coefficients such as age, sex, and environment may be used in determining whether the driver is irritated.

[Process of Driver Condition Estimation Apparatus 5]

When it is determined that the driver is irritated, the control variable changing unit 50b sets the characteristics of the vehicle 3 as in the first embodiment by requesting the ECUs to change control variables. When it is determined that the driver has calmed down, the control variable changing unit 50b resets the characteristics of the vehicle 3.

Figure 15:
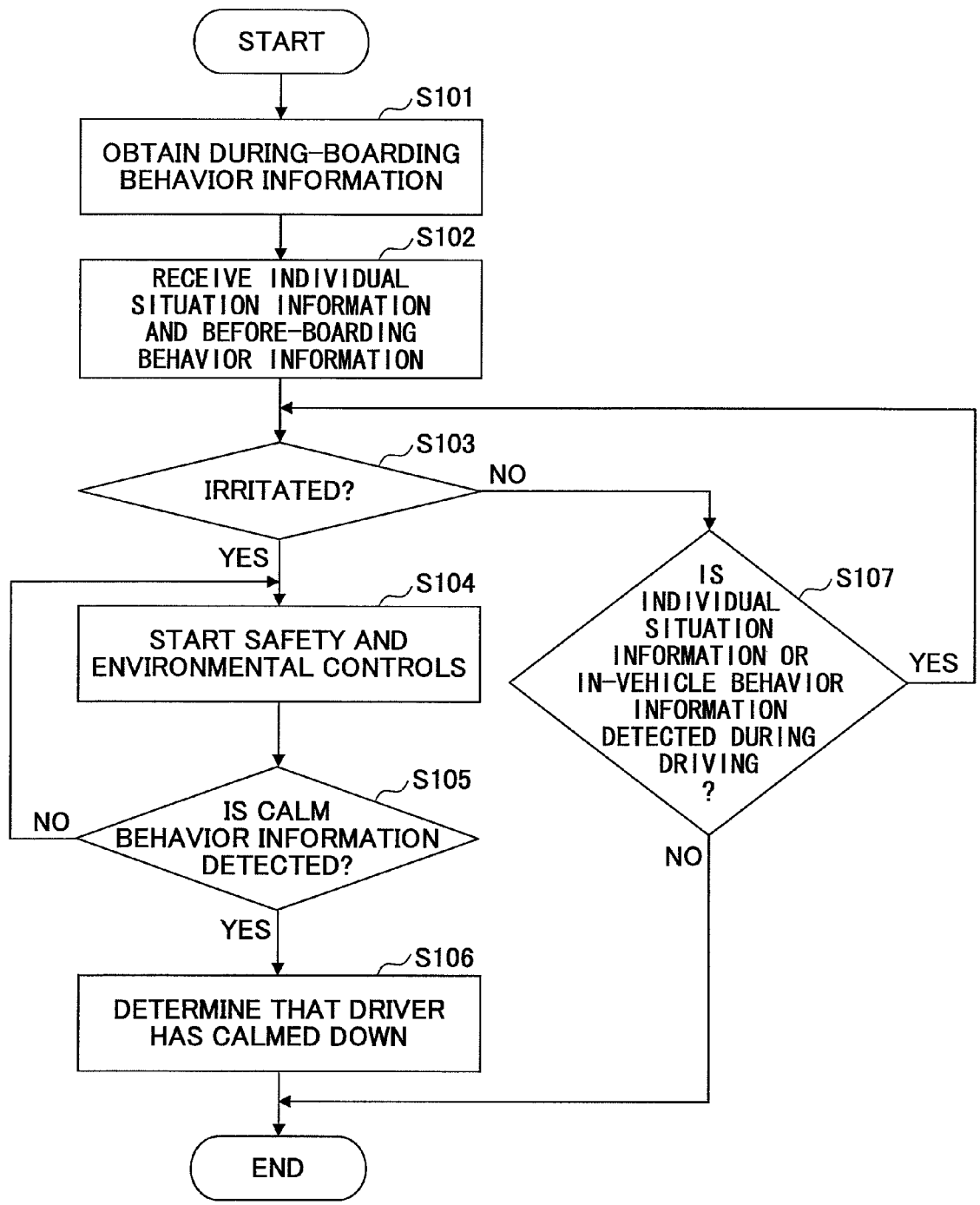
FIG. 15 is a flowchart showing a process performed by a driver condition estimation apparatus according to the second embodiment.

FIG. 15 is a flowchart showing a process performed by the driver condition estimation apparatus 5 according to the second embodiment. In the flowchart shown in FIG. 15, safety and environmental controls are performed according to the individual situation information, the before-boarding behavior information, the during-boarding behavior information, and the in-vehicle behavior information.

When the door is unlocked, i.e., when the driver comes close to the vehicle 3, the driver condition estimating unit 50a obtains during-boarding behavior information (S101).

When the ignition is turned on, the vehicle 3 receives individual situation information and before-boarding behavior information via the information center 2 (S102). Alternatively, the vehicle 3 may be configured to receive the individual situation information and the before-boarding behavior information before the driver reaches the vehicle 3 and the ignition is turned on.

Then, the driver condition estimating unit 50a determines whether the driver is irritated based on the numbers of detected situations and events in the individual situation information, the before-boarding behavior information, and the during-boarding behavior information (S103). For example, the driver condition estimating unit 50a determines that the driver is irritated if the number of detected situations in the individual situation information is two or more, if two or more of the numbers of detected situations or events in the individual situation information, the before-boarding behavior information, and the during-boarding behavior information are greater than or equal to the value L, or if any one of the numbers of detected situations or events is greater than or equal to the value M.

Also, in this embodiment, the driver condition estimating unit 50a may be configured to determine that the driver is irritated if a scheduled arrival time obtained, for example, from the VICS is later than a meeting time extracted from a schedule.

If the driver is not irritated (NO in S103), the driver condition estimating unit 50a does not perform any control while the driver is getting into the vehicle 3, and continues to determine whether individual situation information or in-vehicle behavior information is detected during driving (S107). If none of individual situation information and in-vehicle behavior information is detected (NO in S107), the driver condition estimating unit 50a does not change the characteristics of the vehicle 3.

If individual situation information or in-vehicle behavior information is detected (YES in S107), the driver condition estimating unit 50a returns to step S103 and determines again whether the driver is irritated.

If the driver is irritated (YES in S103), the driver condition estimating unit 50a performs the safety controls I-III and the environmental control (S104).

While the vehicle 3 is running, the driver condition estimating unit 50a determines whether calm behavior information is detected (S105). For example, if the number of detected behavioral events indicating calmness of the driver becomes greater than or equal to a threshold, the driver condition estimating unit 50a determines that the calm behavior information is detected.

If the calm behavior information is detected (YES in S105), the driver condition estimating unit 50a ends the safety controls and the environmental control (S106).

Thus, compared with the first embodiment, the second embodiment makes it possible to more accurately determine whether the driver is irritated based on individual situation information and thereby to control a vehicle in a safe and environmentally-friendly manner.

Third Embodiment

In the first embodiment, at the home 1, whether the driver is irritated is determined based on the behavior of the driver. A third embodiment of the present invention also makes it possible to obtain sleep condition of the driver using configurations similar to those of the first embodiment. In the third embodiment, information regarding sleep condition (physical condition) of the driver is obtained at the home 1 with a configuration similar to that used to detect irritation of the driver. If it is determined based on the sleep condition that the driver is likely to become sleepy (hereafter, simply expressed as "driver is sleepy"), the vehicle characteristics are changed taking into account the sleepiness of the driver to reduce the influence of the sleepiness on driving. Here, only the sleepiness of the driver or both the sleepiness and the irritation of the driver may be detected. In this embodiment, it is assumed that both the sleepiness and the irritation of the driver are detected. The respective configurations of the driver information collecting apparatus 6, the driver condition estimation apparatus 5, and the control system for controlling the vehicle 3 are substantially the same as those shown in FIG. 3, FIG. 6, and FIG. 9, and therefore their descriptions are omitted here.

[Situations Causing Lack of Sleep and Detection of Those Situations]

The information collecting device 60 of the home 1 collects sleepiness factor information affecting the sleep condition of the driver using the electric appliance monitor 63 and the sound collector 64. The information collecting device 60 estimates sleeping time based on operating duration of the fluorescent lamp (from the turn-on time to the turn-off time in the next morning) detected by the electric appliance monitor 63. The sleeping time may be determined by any other method. For example, if the fluorescent lamp is turned off but the television is turned on, the sleeping time may be estimated based on the time when the television is turned off and the time when an electric appliance is turned on in the next morning.

Also, if a microphone is provided in the bedroom, the information collecting device 60 determines the quality of sleep based on the sound volume and cycle of snoring detected by the sound collector 64. Further, the information collecting device 60 determines the number of times, frequency, and volume of night cries of a baby and determines the number of times and volume of noises made by motorcycle gangs.

The information collecting device 60 stores sleepiness factor information regarding sleeping time, snoring, night cries, and noises in the memory 602. FIG. 16 is a table showing exemplary sleepiness factor information stored in the memory 602. For example, every morning, the driver information collecting unit 60a stores sleepiness factor information for determining the sleep condition of the driver in the previous night in the memory 602. In the example shown in FIG. 16, the following sleepiness factors are recorded: "sleeping time: 7 h", "sound information: snoring level 3", and "sound information: ambient noise level 2" (the greater the value, the larger the sound volume).

The driver information collecting unit 60a sends the sleepiness factor information via the information center 2 to the vehicle 3 when the driver leaves the home 1. Based on the sleepiness factor information, the information center 2 or the vehicle 3 determines whether the driver is sleepy. Alternatively, the driver information collecting unit 60a may be configured to determine whether the driver is sleepy based on the sleepiness factor information.

[Process of Determining Whether Driver is Sleepy]

For example, the driver is determined to be sleepy if two or more of the following conditions are met: the sleeping time is less than or equal to a predetermined time period; the snoring level is greater than or equal to a threshold; and the ambient noise level is greater than or equal to a threshold. Instead, the driver may be determined to be sleepy based solely on the sleeping time if it is extremely short. Also, sleepiness factors may be weighted according to their degrees of influence on the sleepiness and the driver may be determined to be sleepy if any one of the weighted sleepiness factors exceeds a threshold. Also, the sleepiness may be defined by several sleepiness levels.

Meanwhile, when the driver is in the vehicle 3, the face camera 54 takes a picture of the face of the driver and determines whether the eyes of the driver are open or closed. The driver condition estimating unit 50a may be configured to determine that the driver is sleepy if the driver's eyes are closed longer than a predetermined period of time. Further, the driver condition estimating unit 50a may be configured to determine whether the driver is sleepy based on the temperature, blood pressure, and perspiration of the driver detected by sensors provided, for example, on the steering wheel.

[Vehicle Characteristics when Driver is Determined to be Sleepy]

Vehicle controls performed when the driver is determined to be sleepy is described below. If the driver is determined to be sleepy, it is preferable to warn the driver to keep him/her awake and to control the vehicle 3 to prevent it from getting out of the lane or colliding with a vehicle ahead.

Referring to FIG. 9, if the driver condition estimating unit 50a determines that the driver is sleepy, the control variable changing unit 50b requests the meter ECU 501 to change control variables via an in-vehicle LAN such as a CAN.

Caution and Warning for Driver

When requested to change control variables, the meter ECU 501 changes the frequency and tone of a warning sound to keep the driver awake. For example, increasing the frequency (e.g., from 0.7 kHz to 1.4 kHz, i.e., from pip---pip---pip to pip-pip-pip) makes it possible to more effectively draw the attention of the driver. Also, it is possible to more effectively draw the attention of the driver by increasing the volume of the warning sound, by increasing the size of a message to be displayed on a navigation screen or a liquid-crystal display, or by increasing the luminance of a warning lamp of the combination panel.

Changing Vehicle Control Variables by Autonomous System

When requested to change control variables, the LKA unit 504 decreases the threshold for outputting a warning sound. When requested, the PCS unit 507 sets the threshold of the TTC for outputting a warning sound longer than normal. Also, the ACC unit 505 sets the distance from a vehicle ahead at the highest one of the three levels or at an even higher level. Meanwhile, the above safety measures may be bothersome for the driver. Therefore, the control variable changing unit 50b may be configured to perform controls as described above after reporting to the driver. If the LKA unit 504, the ACC unit 505, and the PCS unit 507 are turned off by the driver, the control variable changing unit 50b turns on the units after reporting and then starts the vehicle controls.

Also, the control variable changing unit 50b may be configured to cause the air conditioner to reduce the temperature or increase the oxygen concentration to keep the driver awake. With the above configuration, it is possible to determine that the driver is sleepy before the driver starts driving. Therefore, the control variable changing unit 50b may be configured to recline the seat, to move the steering wheel to the highest or lowest position, or to cause the driver to adjust the position of the seat or the steering wheel to keep the driver awake.

When the driver condition estimating unit 50a determines that the driver is irritated, the ECUs also perform the safety controls I-III and the environmental control on the vehicle 3 as in the first and second embodiments. If a vehicle control to be performed when the driver is irritated and a vehicle control to be performed when the driver is sleepy are the same, either one of the vehicle controls is performed.

[Process of Determining Whether Driver is Fully Awake]

If the driver becomes fully awake, vehicle controls are ended. The driver condition estimating unit 50a detects behavior of the driver when getting into the vehicle 3 and during driving, and determines that the driver has become fully awake if an behavioral event indicating that the driver is in normal condition (not sleepy) is detected.

Generally, when not sleepy, the driver operates the steering wheel speedily, keeps a safe distance from a vehicle ahead, quickly responds to a traffic light, and does not change directions frequently with respect to the driving lane. The driver condition estimating unit 50a detects vehicle operations by the driver during driving and determines whether the driver is fully awake. For example, the driver condition estimating unit 50a obtains the steering speed detected by a steering angle sensor, the distance from a vehicle ahead detected by the millimeter wave radar 47, the status of a traffic light and a braking timing, and the deviation of the vehicle 3 from a target traveling line, and records them as wakening behavior information.

When the driver gets into the vehicle 3 and when the driver is in the vehicle 3, the face camera 54 takes a picture of the face of the driver and determines whether the eyes of the driver are open or closed. The driver condition estimating unit 50a determines that the driver is becoming fully awake if the driver's eyes are open longer than a predetermined period of time. The driver condition estimating unit 50a may be configured to gradually end controls according to the length of the period of time for which the driver's eyes are open.

For example, the driver condition estimating unit 50a determines that the driver is fully awake if the number of behavioral events detected as the wakening behavior information becomes greater than or equal to a threshold. Also, the driver condition estimating unit 50a may be configured to gradually end the vehicle controls (vehicle control by autonomous system and warning for the driver) and thereby to gradually reduce the intervention level as the number of behavioral events detected as the wakening behavior information increases.

[Process of Driver Condition Estimation Apparatus 5]

Figure 17:
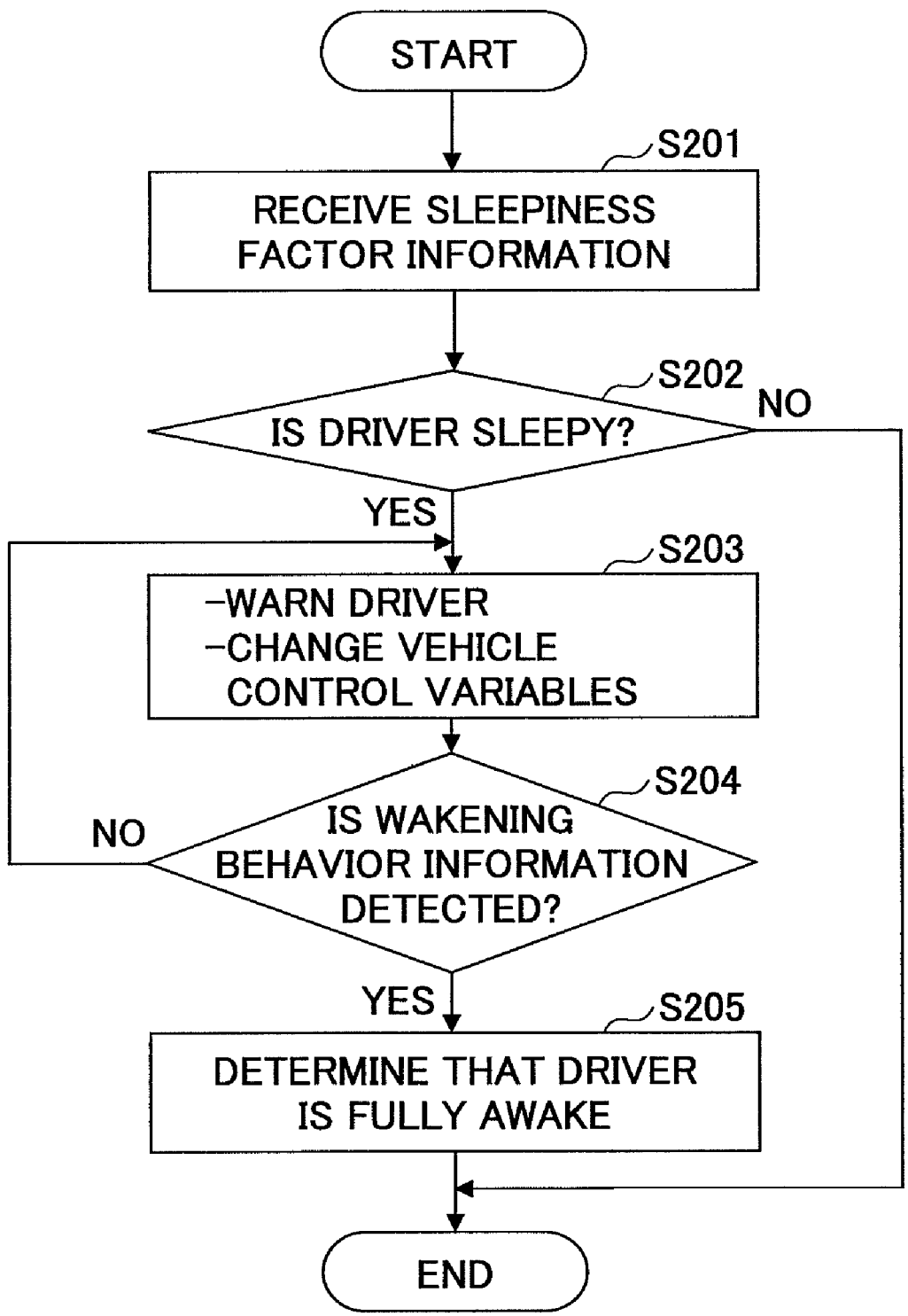
FIG. 17 is a flowchart showing a process performed by a driver condition estimation apparatus according to a third embodiment.

FIG. 17 is a flowchart showing a process performed by the driver condition estimation apparatus 5 according to the third embodiment. The process shown in FIG. 17 is started, for example, when the ignition is turned on.

When the ignition is turned on, the vehicle 3 receives sleepiness factor information via the information center 2 (S201). Alternatively, the vehicle 3 may be configured to receive the sleepiness factor information before the driver reaches the vehicle 3 and the ignition is turned on.

Then, the driver condition estimating unit 50a determines whether the driver is sleepy based on the number of detected sleepiness factors in the sleepiness factor information (S202).

If the driver is not sleepy (NO in S202), the driver condition estimating unit 50a terminates the process. If the driver is sleepy (YES in S202), the control variable changing unit 50b warns the driver and changes vehicle control variables to enable safe driving even when the driver is sleepy (S203).

While the vehicle 3 is running, the driver condition estimating unit 50a determines whether wakening behavior information is detected (S204). For example, if the number of detected behavioral events becomes greater than or equal to a threshold, the driver condition estimating unit 50a determines that the wakening behavior information is detected.

If the wakening behavior information is detected (YES in S204), the control variable changing unit 50b determines that the driver is fully awake and ends the vehicle controls (S205).

Thus, the third embodiment makes it possible to determine whether the driver is sleepy based on the behavior of the driver at the home 1 and to control the vehicle 3 even before the driver starts driving. In other words, the third embodiment makes it possible to determine whether the driver is sleepy at an early stage and thereby to enable the driver to drive safely.

As described above, embodiments of the present invention make it possible to estimate the condition of the driver even before the driver starts driving and thereby to provide appropriate driving assistance from when the driver starts driving. This in turn makes it possible to reduce the influence of the mental condition of the driver on driving.

The present international application claims priority from Japanese Patent Application No. 2006-309460 filed on Nov. 15, 2006, the entire contents of which are hereby incorporated herein by reference.

The invention claimed is:

1. A driver condition estimation apparatus for estimating condition of a driver, comprising:
    an at-home driver information receiving unit configured to receive at-home driver information including at least one of things-forgot-to-bring information, forgot-to-lock information, and forgot-to-turn-off-fluorescent-lamp information obtained at a home of the driver;
    a driver condition estimating unit configured to estimate the condition of the driver before the driver starts driving based on the at-home driver information; and
    a control variable changing unit configured to change control variables of in-vehicle devices based on the condition of the driver estimated by the driver condition estimating unit.

2. The driver condition estimation apparatus as claimed in claim 1, wherein
the at-home driver information includes information regarding sleep of the driver; and
the driver condition estimating unit is configured to estimate sleepiness of the driver based on the at-home driver information.

3. The driver condition estimation apparatus as claimed in claim 1, wherein:
a the driver condition estimating unit is configured to detect operations performed in a vehicle by the driver before starting an engine,
wherein the driver condition estimating unit is configured to estimate the condition of the driver based on the detection results.

4. The driver condition estimation apparatus as claimed in claim 1, wherein
the at-home driver information includes conversation information extracted from a conversation of the driver; and
the driver condition estimating unit is configured to estimate the condition of the driver based on the conversation information.

5. The driver condition estimation apparatus as claimed in claim 1, wherein
the at-home driver information includes scheduled time information and scheduled event information extracted from a schedule of the driver; and
the driver condition estimating unit is configured to estimate the condition of the driver based on the scheduled event information.

6. The driver condition estimation apparatus as claimed in claim 1, wherein
the at-home driver information includes email information extracted from an email message sent or received by the driver; and
the driver condition estimating unit is configured to estimate the condition of the driver based on the email information.

7. The driver condition estimation apparatus as claimed in claim 3, wherein the driver condition estimating unit is configured to detect throwing of baggage, a door opening/closing speed higher than or equal to a threshold, or a switch operation error.

8. A server, comprising:
an at-home driver information receiving unit configured to receive at-home driver information including at least one of things-forgot-to-bring information, forgot-to-lock information, and forgot-to-turn-off-fluorescent-lamp information obtained at a home of a driver;
a driver condition estimating unit configured to estimate condition of the driver based on the at-home driver information; and
a transmitting unit configured to transmit the condition of the driver estimated by the driver condition estimating unit to a vehicle.

9. A driver information collecting apparatus, comprising:
a sensor configured to obtain information on a driver at a home of the driver;
a driver information collecting unit configured to collect the information on the driver including at least one of things-forgot-to-bring information, forgot-to-lock information, and forgot-to-turn-off-fluorescent-lamp information obtained by the sensor; and
a transmitting unit configured to transmit the information on the driver collected by the driver information collecting unit to a vehicle.

10. A driver condition estimation system for estimating condition of a driver, comprising:
a home of the driver; and
a vehicle, wherein
the home includes
a sensor configured to obtain at-home driver information on the driver,
a driver information collecting unit configured to collect the at-home driver information including at least one of things-forgot-to-bring information, forgot-to-lock information, and forgot-to-turn-off-fluorescent-lamp information obtained by the sensor, and
a transmitting unit configured to transmit the at-home driver information to the vehicle; and
the vehicle includes
a receiving unit configured to receive the at-home driver information, and
a driver condition estimating unit configured to estimate the condition of the driver before the driver starts driving based on the at-home driver information or operations of in-vehicle devices performed by the driver before starting an engine.

* * * * *